United States Patent
Lee et al.

(10) Patent No.: US 9,737,272 B2
(45) Date of Patent: Aug. 22, 2017

(54) CHARGED PARTICLE CANCER THERAPY BEAM STATE DETERMINATION APPARATUS AND METHOD OF USE THEREOF

(71) Applicants: W. Davis Lee, Newburyport, MA (US); Susan L. Michaud, Brewster, MA (US); Daniel J. Raymond, Windham, NH (US); Mark R. Amato, South Hamilton, MA (US)

(72) Inventors: W. Davis Lee, Newburyport, MA (US); Susan L. Michaud, Brewster, MA (US); Daniel J. Raymond, Windham, NH (US); Mark R. Amato, South Hamilton, MA (US)

(*) Notice: Subject to any disclaimer, the term of this patent is extended or adjusted under 35 U.S.C. 154(b) by 0 days.

(21) Appl. No.: 15/207,309

(22) Filed: Jul. 11, 2016

(65) Prior Publication Data
US 2016/0317836 A1 Nov. 3, 2016

Related U.S. Application Data

(63) Continuation-in-part of application No. 15/167,617, filed on May 27, 2016, which is a continuation-in-part
(Continued)

(51) Int. Cl.
*A61N 5/00* (2006.01)
*A61B 6/00* (2006.01)
(Continued)

(52) U.S. Cl.
CPC ............ *A61B 6/4216* (2013.01); *A61B 6/032* (2013.01); *A61B 6/4258* (2013.01);
(Continued)

(58) Field of Classification Search
None
See application file for complete search history.

(56) References Cited

U.S. PATENT DOCUMENTS 2,306,875 A 12/1942 Fremlin
2,533,688 A 12/1950 Quam
(Continued)

FOREIGN PATENT DOCUMENTS

EP 1683545 A2 7/2006
GB 1270619 A 4/1972
(Continued)

OTHER PUBLICATIONS

Adams, "Electrostatic cylinder lenses II: Three Element Einzel Lenses", Journal, Feb. 1, 1972, pp. 150-155, XP002554355, vol. 5 No. 2, Journal of Physics E.
(Continued)

*Primary Examiner* — Andrew Smyth
(74) *Attorney, Agent, or Firm* — Kevin Hazen

(57) ABSTRACT

The invention comprises an apparatus and method of use thereof for determining a charged particle beam state after passage through a final beam modification insert and prior to entering a patient, such as in cancer treatment or tomographic imaging. The insert comprises a range shifter, a known energy absorber, a ridge filter, a focal length altering insert, an aperture defining element, a compensator, and/or a patient specific beam modifier. The monitoring element comprises one or more sheets, configured to emit photons upon passage therethrough of the charged particle beam, where the emitted photons are detected, tested, such as against a predetermined cancer treatment plan, and/or used to aid in three dimensional tomographic image generation.

17 Claims, 16 Drawing Sheets

Related U.S. Application Data of application No. 15/152,479, filed on May 11, 2016, which is a continuation-in-part of application No. 14/216,788, filed on Mar. 17, 2014, now Pat. No. 9,682,254, which is a continuation-in-part of application No. 13/087,096, filed on Apr. 14, 2011, now Pat. No. 9,044,600, said application No. 14/216,788 is a continuation-in-part of application No. 13/788,890, filed on Mar. 7, 2013, now Pat. No. 8,907,309, said application No. 15/152,479 is a continuation-in-part of application No. 14/952,817, filed on Nov. 25, 2015, which is a continuation-in-part of application No. 14/293,861, filed on Jun. 2, 2014, now Pat. No. 9,498,649, which is a continuation-in-part of application No. 12/985,039, filed on Jan. 5, 2011, now Pat. No. 8,598,543, said application No. 15/152,479 is a continuation-in-part of application No. 14/860,577, filed on Sep. 21, 2015, now Pat. No. 9,543,106, which is a continuation of application No. 14/223,289, filed on Mar. 24, 2014, now Pat. No. 9,177,751, which is a continuation-in-part of application No. 14/216,788, filed on Mar. 17, 2014, now Pat. No. 9,682,254, which is a continuation-in-part of application No. 12/985,039, filed on Jan. 5, 2011, now Pat. No. 8,598,543, said application No. 15/152,479 is a continuation-in-part of application No. 15/073,471, filed on Mar. 17, 2016, said application No. 15/167,617 is a continuation-in-part of application No. 14/860,577, filed on Sep. 21, 2015, now Pat. No. 9,543,106, which is a continuation of application No. 14/223,289, filed on Mar. 24, 2014, now Pat. No. 9,177,751, which is a continuation-in-part of application No. 14/216,788, filed on Mar. 17, 2014, now Pat. No. 9,682,254, which is a continuation-in-part of application No. 13/572,542, filed on Aug. 10, 2012, now Pat. No. 9,056,199, which is a continuation-in-part of application No. 12/425,683, filed on Apr. 17, 2009, now Pat. No. 7,939,809.

(60) Provisional application No. 61/324,776, filed on Apr. 16, 2010, provisional application No. 62/304,839, filed on Mar. 7, 2016, provisional application No. 61/055,395, filed on May 22, 2008.

(51) Int. Cl.
- A61N 5/10 (2006.01)
- G21K 5/04 (2006.01)
- A61B 6/03 (2006.01)
- G21K 1/08 (2006.01)

(52) U.S. Cl.
CPC ......... *A61N 5/1044* (2013.01); *A61N 5/1067* (2013.01); *A61N 5/1077* (2013.01); *A61N 5/1082* (2013.01); *G21K 1/08* (2013.01); *G21K 5/04* (2013.01); *A61B 6/5205* (2013.01); *A61N 5/107* (2013.01); *A61N 2005/1054* (2013.01); *A61N 2005/1087* (2013.01); *A61N 2005/1095* (2013.01); *A61N 2005/1097* (2013.01)

(56) References Cited

U.S. PATENT DOCUMENTS

| | | |
|---|---|---|
| 2,613,726 A | 10/1952 | Paatero |
| 2,790,902 A | 4/1957 | Wright |
| 3,128,405 A | 4/1964 | Lambertson |
| 3,412,337 A | 11/1968 | Lothrop |
| 3,582,650 A | 6/1971 | Avery |
| 3,585,386 A | 6/1971 | Horton |
| 3,655,968 A | 4/1972 | Moore |
| 3,867,705 A | 2/1975 | Hudson |
| 3,882,339 A | 5/1975 | Rate |
| 3,906,280 A | 9/1975 | Andelfinger |
| 3,911,280 A | 10/1975 | Hyman et al. |
| 3,986,026 A * | 10/1976 | Martin ............... A61B 6/00 250/306 |
| 4,002,912 A | 1/1977 | Johnson |
| 4,344,011 A | 8/1982 | Hayashi |
| 4,472,822 A | 9/1984 | Swift |
| 4,607,380 A | 8/1986 | Oliver |
| 4,622,687 A | 11/1986 | Whitaker |
| 4,705,955 A | 11/1987 | Mileikowsky |
| 4,726,046 A | 2/1988 | Nunan |
| 4,730,353 A | 3/1988 | Ono |
| 4,740,758 A | 4/1988 | Ries |
| 4,843,333 A | 6/1989 | Marsing et al. |
| 4,868,844 A | 9/1989 | Nunan |
| 4,870,287 A | 9/1989 | Cole |
| 4,908,580 A | 3/1990 | Yamada et al. |
| 4,989,225 A | 1/1991 | Gupta et al. |
| 4,992,746 A | 2/1991 | Martin |
| 4,996,496 A | 2/1991 | Kitamura et al. |
| 4,998,258 A | 3/1991 | Ikeda |
| 5,010,562 A | 4/1991 | Hernandez et al. |
| 5,017,789 A | 5/1991 | Young |
| 5,017,882 A | 5/1991 | Finlan |
| 5,039,867 A | 8/1991 | Nishihara |
| 5,046,078 A | 9/1991 | Hernandez et al. |
| 5,073,913 A | 12/1991 | Martin |
| 5,098,158 A | 3/1992 | Palarski |
| 5,101,169 A | 3/1992 | Gomei |
| 5,117,194 A | 5/1992 | Nakanishi |
| 5,168,241 A | 12/1992 | Hirota |
| 5,168,514 A | 12/1992 | Horton |
| 5,177,448 A | 1/1993 | Ikeguchi |
| 5,216,377 A | 6/1993 | Nakata |
| 5,260,581 A | 11/1993 | Lesyna |
| 5,285,166 A | 2/1994 | Hiramoto |
| 5,349,198 A | 9/1994 | Takanaka |
| 5,363,008 A | 11/1994 | Hiramoto |
| 5,388,580 A | 2/1995 | Sullivan |
| 5,402,462 A | 3/1995 | Nobuta |
| 5,423,328 A | 6/1995 | Gavish |
| 5,440,133 A | 8/1995 | Moyers |
| 5,483,129 A | 1/1996 | Yamamoto |
| 5,511,549 A | 4/1996 | Legg |
| 5,538,494 A | 7/1996 | Matsuda |
| 5,568,109 A | 10/1996 | Takayama |
| 5,576,549 A | 11/1996 | Hell |
| 5,576,602 A | 11/1996 | Hiramoto |
| 5,585,642 A | 12/1996 | Britton |
| 5,595,191 A | 1/1997 | Kirk |
| 5,600,213 A | 2/1997 | Hiramoto |
| 5,626,682 A | 5/1997 | Kobari |
| 5,633,907 A | 5/1997 | Gravelle |
| 5,642,302 A | 6/1997 | Dumont |
| 5,659,223 A | 8/1997 | Goodman |
| 5,661,366 A | 8/1997 | Hirota |
| 5,668,371 A | 9/1997 | Deasy |
| 5,698,954 A | 12/1997 | Hirota |
| 5,760,395 A | 6/1998 | Johnstone |
| 5,789,875 A | 8/1998 | Hiramoto |
| 5,790,997 A | 8/1998 | Ruehl |
| 5,818,058 A | 10/1998 | Nakanishi |
| 5,820,320 A | 10/1998 | Kobari |
| 5,825,845 A | 10/1998 | Blair |
| 5,825,847 A | 10/1998 | Ruth |
| 5,854,531 A | 12/1998 | Young |
| 5,866,912 A | 2/1999 | Slater |
| 5,895,926 A | 4/1999 | Britton |
| 5,907,595 A | 5/1999 | Sommerer |
| 5,917,293 A | 6/1999 | Saito |
| 5,949,080 A | 9/1999 | Ueda et al. |
| 5,969,367 A | 10/1999 | Hiramoto |
| 5,986,274 A | 11/1999 | Akiyama |

(56) References Cited

U.S. PATENT DOCUMENTS

| | | |
|---|---|---|
| 5,993,373 A | 11/1999 | Nonaka |
| 6,008,499 A | 12/1999 | Hiramoto |
| 6,034,377 A | 3/2000 | Pu |
| 6,057,655 A | 5/2000 | Jongen |
| 6,087,670 A | 7/2000 | Hiramoto |
| 6,087,672 A | 7/2000 | Matsuda |
| 6,148,058 A | 11/2000 | Dobbs |
| 6,201,851 B1 | 3/2001 | Piestrup et al. |
| 6,207,952 B1 | 3/2001 | Kan |
| 6,218,675 B1 | 4/2001 | Akiyama |
| 6,236,043 B1 | 5/2001 | Tadokoro |
| 6,265,837 B1 | 7/2001 | Akiyama |
| 6,282,263 B1 | 8/2001 | Arndt |
| 6,298,260 B1 | 10/2001 | Sontag |
| 6,316,776 B1 | 11/2001 | Hiramoto |
| 6,322,249 B1 | 11/2001 | Wofford |
| 6,335,535 B1 | 1/2002 | Miyake |
| 6,339,635 B1 | 1/2002 | Schardt |
| 6,356,617 B1 | 3/2002 | Besch |
| 6,365,894 B2 | 4/2002 | Tadokoro |
| 6,421,416 B1 | 7/2002 | Sliski |
| 6,433,336 B1 | 8/2002 | Jongen |
| 6,433,349 B2 | 8/2002 | Akiyama |
| 6,433,494 B1 | 8/2002 | Kulish |
| 6,437,513 B1 | 8/2002 | Stelzer |
| 6,444,990 B1 | 9/2002 | Morgan |
| 6,462,490 B1 | 10/2002 | Matsuda |
| 6,470,068 B2 | 10/2002 | Cheng |
| 6,472,834 B2 | 10/2002 | Hiramoto |
| 6,476,403 B1 | 11/2002 | Dolinskii |
| 6,545,436 B1 | 4/2003 | Gary |
| 6,560,354 B1 | 5/2003 | Maurer, Jr. |
| 6,580,084 B1 | 6/2003 | Hiramoto |
| 6,597,005 B1 | 7/2003 | Badura |
| 6,600,164 B1 | 7/2003 | Badura |
| 6,614,038 B1 | 9/2003 | Brand |
| 6,617,598 B1 | 9/2003 | Matsuda |
| 6,626,842 B2 | 9/2003 | Oka |
| 6,635,882 B1 | 10/2003 | Pavlovic |
| 6,639,234 B1 | 10/2003 | Badura |
| 6,670,618 B1 | 12/2003 | Hartmann |
| 6,683,318 B1 | 1/2004 | Haberer |
| 6,683,426 B1 | 1/2004 | Kleeven |
| 6,710,362 B2 | 3/2004 | Kraft |
| 6,717,162 B1 | 4/2004 | Jongen |
| 6,725,078 B2 | 4/2004 | Bucholz |
| 6,730,921 B2 | 5/2004 | Kraft |
| 6,736,831 B1 | 5/2004 | Hartmann |
| 6,745,072 B1 | 6/2004 | Badura |
| 6,774,383 B2 | 8/2004 | Norimine |
| 6,777,700 B2 | 8/2004 | Yanagisawa |
| 6,785,359 B2 | 8/2004 | Lemaitre |
| 6,787,771 B2 | 9/2004 | Bashkirov |
| 6,792,078 B2 | 9/2004 | Kato |
| 6,799,068 B1 | 9/2004 | Hartmann |
| 6,800,866 B2 | 10/2004 | Amemiya |
| 6,803,591 B2 | 10/2004 | Muramatsu |
| 6,809,325 B2 | 10/2004 | Dahl |
| 6,819,743 B2 | 11/2004 | Kato |
| 6,822,244 B2 | 11/2004 | Beloussov |
| 6,823,045 B2 | 11/2004 | Kato |
| 6,838,676 B1 | 1/2005 | Jackson |
| 6,842,502 B2 | 1/2005 | Jaffray |
| 6,859,741 B2 | 2/2005 | Haberer |
| 6,862,469 B2 | 3/2005 | Bucholz |
| 6,873,123 B2 | 3/2005 | Marchand |
| 6,881,970 B2 | 4/2005 | Akiyama |
| 6,891,177 B1 | 5/2005 | Kraft |
| 6,897,451 B2 | 5/2005 | Kaercher |
| 6,900,446 B2 | 5/2005 | Akiyama |
| 6,903,351 B1 | 6/2005 | Akiyama |
| 6,903,356 B2 | 6/2005 | Muramatsu |
| 6,931,100 B2 | 8/2005 | Kato |
| 6,936,832 B2 | 8/2005 | Norimine |
| 6,937,696 B1 | 8/2005 | Mostafavi |
| 6,953,943 B2 | 10/2005 | Yanagisawa |
| 6,979,832 B2 | 12/2005 | Yanagisawa |
| 6,984,835 B2 | 1/2006 | Harada |
| 6,992,312 B2 | 1/2006 | Yanagisawa |
| 6,998,258 B1 | 2/2006 | Kesseler |
| 7,012,267 B2 | 3/2006 | Moriyama |
| 7,026,636 B2 | 4/2006 | Yanagisawa |
| 7,030,396 B2 | 4/2006 | Muramatsu |
| 7,045,781 B2 | 5/2006 | Adamec |
| 7,049,613 B2 | 5/2006 | Yanagisawa |
| 7,053,389 B2 | 5/2006 | Yanagisawa |
| 7,054,801 B2 | 5/2006 | Sakamoto |
| 7,058,158 B2 | 6/2006 | Sako |
| 7,060,997 B2 | 6/2006 | Norimine |
| 7,071,479 B2 | 7/2006 | Yanagisawa |
| 7,081,619 B2 | 7/2006 | Bashkirov |
| 7,084,410 B2 | 8/2006 | Beloussov |
| 7,091,478 B2 | 8/2006 | Haberer |
| 7,102,144 B2 | 9/2006 | Matsuda |
| 7,109,505 B1 | 9/2006 | Sliski |
| 7,122,811 B2 | 10/2006 | Matsuda |
| 7,141,810 B2 | 11/2006 | Kakiuchi |
| 7,154,107 B2 | 12/2006 | Yanagisawa |
| 7,154,108 B2 | 12/2006 | Tadokoro |
| 7,173,264 B2 | 2/2007 | Moriyama |
| 7,173,265 B2 | 2/2007 | Miller |
| 7,193,227 B2 | 3/2007 | Hiramoto |
| 7,199,382 B2 | 4/2007 | Rigney |
| 7,208,748 B2 | 4/2007 | Sliski |
| 7,212,608 B2 | 5/2007 | Nagamine |
| 7,212,609 B2 | 5/2007 | Nagamine |
| 7,227,161 B2 | 6/2007 | Matsuda |
| 7,247,869 B2 | 7/2007 | Tadokoro |
| 7,252,745 B2 | 8/2007 | Gorokhovsky |
| 7,259,529 B2 | 8/2007 | Tanaka |
| 7,262,424 B2 | 8/2007 | Moriyama |
| 7,274,018 B2 | 9/2007 | Adamec |
| 7,274,025 B2 | 9/2007 | Berdermann |
| 7,280,633 B2 | 10/2007 | Cheng |
| 7,297,967 B2 | 11/2007 | Yanagisawa |
| 7,301,162 B2 | 11/2007 | Matsuda |
| 7,307,264 B2 | 12/2007 | Brusasco |
| 7,310,404 B2 | 12/2007 | Tashiro |
| 7,315,606 B2 | 1/2008 | Tsujii |
| 7,319,231 B2 | 1/2008 | Moriyama |
| 7,342,516 B2 | 3/2008 | Kato et al. |
| 7,345,291 B2 | 3/2008 | Kats |
| 7,345,292 B2 | 3/2008 | Moriyama |
| 7,349,522 B2 | 3/2008 | Yan et al. |
| 7,351,988 B2 | 4/2008 | Naumann |
| 7,355,189 B2 | 4/2008 | Yanagisawa |
| 7,356,112 B2 | 4/2008 | Brown |
| 7,368,740 B2 | 5/2008 | Beloussov |
| 7,372,053 B2 | 5/2008 | Yamashita |
| 7,378,672 B2 | 5/2008 | Harada |
| 7,381,979 B2 | 6/2008 | Yamashita |
| 7,385,203 B2 | 6/2008 | Nakayama |
| 7,394,082 B2 | 7/2008 | Fujimaki |
| 7,397,054 B2 | 7/2008 | Natori |
| 7,397,901 B1 | 7/2008 | Johnsen |
| 7,402,822 B2 | 7/2008 | Guertin |
| 7,402,823 B2 | 7/2008 | Guertin |
| 7,402,824 B2 | 7/2008 | Guertin |
| 7,402,963 B2 | 7/2008 | Sliski |
| 7,425,717 B2 | 9/2008 | Matsuda |
| 7,432,516 B2 | 10/2008 | Peggs |
| 7,439,528 B2 | 10/2008 | Nishiuchi |
| 7,446,490 B2 | 11/2008 | Jongen |
| 7,449,701 B2 | 11/2008 | Fujimaki |
| 7,453,076 B2 | 11/2008 | Welch et al. |
| 7,456,415 B2 | 11/2008 | Yanagisawa |
| 7,456,591 B2 | 11/2008 | Jongen |
| 7,465,944 B2 | 12/2008 | Ueno |
| 7,471,765 B2 | 12/2008 | Jaffray |
| 7,476,883 B2 | 1/2009 | Nutt |
| 7,492,858 B2 | 2/2009 | Partain |
| 7,531,818 B2 | 5/2009 | Brahme |
| 7,555,103 B2 | 6/2009 | Johnsen |
| 7,560,717 B2 | 7/2009 | Matsuda |

(56) References Cited

U.S. PATENT DOCUMENTS

| | | |
|---|---|---|
| 7,576,342 B2 | 8/2009 | Hiramoto |
| 7,586,112 B2 | 9/2009 | Chiba |
| 7,589,334 B2 | 9/2009 | Hiramoto |
| 7,626,347 B2 | 12/2009 | Sliski |
| 7,634,057 B2 | 12/2009 | Ein-Gal |
| 7,659,521 B2 | 2/2010 | Pedroni |
| 7,668,585 B2 | 2/2010 | Green |
| 7,692,168 B2 | 4/2010 | Moriyama |
| 7,701,677 B2 | 4/2010 | Schultz |
| 7,709,818 B2 | 5/2010 | Matsuda |
| 7,718,982 B2 | 5/2010 | Sliski |
| 7,728,311 B2 | 6/2010 | Gall |
| 7,729,469 B2 | 6/2010 | Kobayashi |
| 7,741,623 B2 | 6/2010 | Sommer |
| 7,755,305 B2 | 7/2010 | Umezawa |
| 7,772,577 B2 | 8/2010 | Saito |
| 7,796,730 B2 | 9/2010 | Marash |
| 7,801,277 B2 | 9/2010 | Zou |
| 7,807,982 B2 | 10/2010 | Nishiuchi |
| 7,817,774 B2 | 10/2010 | Partain |
| 7,817,778 B2 | 10/2010 | Nord |
| 7,825,388 B2 | 11/2010 | Nihongi |
| 7,826,592 B2 | 11/2010 | Jaffray |
| 7,826,593 B2 | 11/2010 | Svensson |
| 7,834,336 B2 | 11/2010 | Boeh |
| 7,838,855 B2 | 11/2010 | Fujii |
| 7,848,488 B2 | 12/2010 | Mansfield |
| 7,860,216 B2 | 12/2010 | Jongen |
| 7,875,868 B2 | 1/2011 | Moriyama |
| 7,894,574 B1 | 2/2011 | Nord |
| 7,906,769 B2 | 3/2011 | Blasche |
| 7,919,765 B2 | 4/2011 | Timmer |
| 7,939,809 B2 | 5/2011 | Balakin |
| 7,940,891 B2 | 5/2011 | Star-Lack |
| 7,940,894 B2 | 5/2011 | Balakin |
| 7,943,913 B2 | 5/2011 | Balakin |
| 7,953,205 B2 | 5/2011 | Balakin |
| 7,961,844 B2 | 6/2011 | Takeda |
| 7,977,656 B2 | 7/2011 | Fujimaki |
| 7,982,198 B2 | 7/2011 | Nishiuchi |
| 7,987,053 B2 | 7/2011 | Schaffner |
| 7,995,813 B2 | 8/2011 | Foshee |
| 8,002,465 B2 | 8/2011 | Ahn |
| 8,003,964 B2 | 8/2011 | Stark |
| 8,009,804 B2 | 8/2011 | Siljamaki |
| 8,045,679 B2 | 10/2011 | Balakin |
| 8,067,748 B2 | 11/2011 | Balakin |
| 8,089,054 B2 | 1/2012 | Balakin |
| 8,093,564 B2 | 1/2012 | Balakin |
| 8,139,712 B2 | 3/2012 | Kojima |
| 8,309,941 B2 | 11/2012 | Balakin |
| 8,374,314 B2 | 2/2013 | Balakin |
| 2001/0009267 A1 | 7/2001 | Tadokoro |
| 2003/0141460 A1 | 7/2003 | Kraft |
| 2003/0163015 A1 | 8/2003 | Yanagisawa |
| 2003/0164459 A1 | 9/2003 | Schardt |
| 2004/0000650 A1* | 1/2004 | Yanagisawa ......... A61N 5/1042 250/492.3 |
| 2004/0022361 A1 | 2/2004 | Lemaitre |
| 2004/0062354 A1 | 4/2004 | Kato |
| 2004/0155206 A1 | 8/2004 | Marchand |
| 2004/0184583 A1 | 9/2004 | Nagamine et al. |
| 2004/0200983 A1* | 10/2004 | Fujimaki ................ A61N 5/10 250/492.3 |
| 2004/0218725 A1 | 11/2004 | Radley |
| 2004/0227074 A1 | 11/2004 | Benveniste et al. |
| 2004/0254492 A1 | 12/2004 | Zhang |
| 2005/0017193 A1 | 1/2005 | Jackson |
| 2005/0087700 A1* | 4/2005 | Tadokoro ............. A61N 5/1048 250/492.21 |
| 2005/0099145 A1 | 5/2005 | Nishiuchi et al. |
| 2005/0148808 A1 | 7/2005 | Cameron |
| 2005/0161618 A1 | 7/2005 | Pedroni |
| 2005/0167610 A1 | 8/2005 | Tajima |
| 2005/0211905 A1 | 9/2005 | Stark |
| 2005/0238134 A1 | 10/2005 | Brusasco |
| 2005/0269497 A1 | 12/2005 | Jongen |
| 2005/0284233 A1 | 12/2005 | Teraura et al. |
| 2006/0050848 A1 | 3/2006 | Vilsmeier |
| 2006/0106301 A1 | 5/2006 | Kats |
| 2006/0163495 A1 | 7/2006 | Hiramoto |
| 2006/0171508 A1 | 8/2006 | Noda |
| 2006/0180158 A1 | 8/2006 | McKnight et al. |
| 2006/0226372 A1 | 10/2006 | Yanagisawa |
| 2006/0255285 A1 | 11/2006 | Jongen |
| 2006/0262898 A1 | 11/2006 | Partain |
| 2007/0018121 A1 | 1/2007 | Leyman |
| 2007/0027389 A1 | 2/2007 | Wesse |
| 2007/0040115 A1 | 2/2007 | Publicover |
| 2007/0051905 A1 | 3/2007 | Fujimaki et al. |
| 2007/0093723 A1 | 4/2007 | Keall |
| 2007/0121788 A1 | 5/2007 | Mildner |
| 2007/0170994 A1 | 7/2007 | Peggs |
| 2007/0181815 A1* | 8/2007 | Ebstein .................. G01T 1/02 250/370.11 |
| 2007/0189461 A1 | 8/2007 | Sommer |
| 2007/0211854 A1 | 9/2007 | Koshnitsky et al. |
| 2007/0215819 A1 | 9/2007 | Hiramoto |
| 2007/0228291 A1 | 10/2007 | Hiramoto |
| 2007/0228304 A1 | 10/2007 | Nishiuchi |
| 2007/0269000 A1 | 11/2007 | Partain et al. |
| 2008/0023644 A1 | 1/2008 | Pedroni |
| 2008/0067405 A1 | 3/2008 | Nihongi et al. |
| 2008/0093567 A1 | 4/2008 | Gall |
| 2008/0139955 A1 | 6/2008 | Hansmann |
| 2008/0191142 A1 | 8/2008 | Pedroni |
| 2008/0267352 A1 | 10/2008 | Aoi |
| 2008/0290297 A1 | 11/2008 | Blasche et al. |
| 2008/0317202 A1 | 12/2008 | Partain et al. |
| 2009/0096179 A1 | 4/2009 | Stark |
| 2009/0140672 A1 | 6/2009 | Gall |
| 2009/0168960 A1 | 7/2009 | Jongen |
| 2009/0184263 A1 | 7/2009 | Moriyama |
| 2009/0189095 A1 | 7/2009 | Flynn |
| 2009/0200483 A1 | 8/2009 | Gall |
| 2009/0236545 A1 | 9/2009 | Timmer |
| 2009/0261248 A1 | 10/2009 | Glavish et al. |
| 2009/0283704 A1 | 11/2009 | Nishiuchi |
| 2009/0289194 A1 | 11/2009 | Saito |
| 2009/0304153 A1 | 12/2009 | Amelia |
| 2009/0314960 A1 | 12/2009 | Balakin |
| 2009/0314961 A1 | 12/2009 | Balakin |
| 2010/0001212 A1 | 1/2010 | Nishiuchi |
| 2010/0006106 A1 | 1/2010 | Balakin |
| 2010/0008468 A1 | 1/2010 | Balakin |
| 2010/0008469 A1 | 1/2010 | Balakin |
| 2010/0027745 A1 | 2/2010 | Balakin |
| 2010/0033115 A1 | 2/2010 | Cleland |
| 2010/0045213 A1 | 2/2010 | Sliski |
| 2010/0059688 A1 | 3/2010 | Claereboudt |
| 2010/0060209 A1 | 3/2010 | Balakin |
| 2010/0090122 A1 | 4/2010 | Balakin |
| 2010/0091948 A1 | 4/2010 | Balakin |
| 2010/0128846 A1 | 5/2010 | Balakin |
| 2010/0163726 A1* | 7/2010 | Shimada ................ A61B 3/12 250/306 |
| 2010/0230617 A1 | 9/2010 | Gall |
| 2010/0272241 A1 | 10/2010 | Amelia |
| 2010/0308235 A1 | 12/2010 | Sliski |
| 2011/0073778 A1 | 3/2011 | Natori |
| 2011/0080172 A1 | 4/2011 | Banning-Geertsma |
| 2011/0089329 A1 | 4/2011 | Jongen |
| 2011/0127443 A1 | 6/2011 | Comer |
| 2011/0137159 A1 | 6/2011 | Jongen |
| 2011/0147608 A1 | 6/2011 | Balakin |
| 2011/0174984 A1 | 7/2011 | Balakin |
| 2011/0178359 A1 | 7/2011 | Hirschman et al. |
| 2011/0186720 A1 | 8/2011 | Jongen |
| 2011/0233423 A1 | 9/2011 | Balakin |
| 2011/2033423 | 9/2011 | Balakin |
| 2011/0278477 A1 | 11/2011 | Balakin |
| 2011/0284760 A1 | 11/2011 | Balakin |
| 2011/0284762 A1 | 11/2011 | Balakin |
| 2011/0313232 A1 | 12/2011 | Balakin |

(56) References Cited

U.S. PATENT DOCUMENTS

2012/0043472 A1  2/2012  Balakin
2012/0205551 A1  8/2012  Balakin
2012/0209109 A1  8/2012  Balakin

FOREIGN PATENT DOCUMENTS

| WO | WO 99/53998 A1 | 10/1999 |
| WO | WO 2007014026 A2 | 1/2007 |
| WO | WO 2008/044194 A2 | 4/2008 |
| WO | WO 2009/142546 A2 | 11/2009 |
| WO | WO 2009/142550 A2 | 11/2009 |
| WO | WO2010/101489 A2 | 9/2010 |

OTHER PUBLICATIONS

Amaldi, "A Hospital-Based Hadrontherapy Complex", Journal, Jun. 27, 1994, pp. 49-51, XP002552288, Proceedings of EPAC 94, London, England.
Arimoto, "A Study of the PRISM-FFAG Magnet", Journal, Oct. 18, 2004,Oct. 22, 2004, pp. 243-245, XP002551810, Proceedings of Cyclotron 2004 Conference, Tokyo, Japan.
Biophysics Group et al. "Design, Construction and First Experiment of a Magnetic Scanning System for Therapy, Radiobiological Experiment on the Radiobiological Action of Carbon, Oxygen and Neon" GSI Report, Gessellschaft fur Schwerionenforschung MBH. vol. GSI-91-18, Jun. 1, 1991, pp. 1-31.
Blackmore, "Operation of the TRIUMF Proton Therapy Facility", Book, May 12, 1997, pp. 3831-3833, XP010322373, vol. 3, Proceedings of the 1997 Particle Accelerator Conference, NJ, USA.
Bryant, "Proton-Ion Medical Machine Study (PIMMS) Part II", Book, Jul. 27, 2000, p. 23,p. 228,pp. 289-290, XP002551811, European Organisation for Nuclear Research Cern-Ps Division, Geneva, Switzerland.
Craddock, "New Concepts in FFAG Design for Secondary Beam Facilities and other Applications", Journal, May 16, 2005,May 20, 2005, pp. 261-265, XP002551806, Proceedings of 2005 Particle Accelerator Conference, Knoxville, Tennessee, USA.
Dzhelepov, "Use of USSR Proton Accelerators for Medical Purposes", Journal,Jun. 1973, pp. 268-270, vol. ns-2—No. 3, XP002553045, IEEE Transactions on Nuclear Science USA, USA.
Endo, "Medical Synchrotron for Proton Therapy" Journal, Jun. 7, 1988,Jun. 11, 1988, pp. 1459-1461, XP002551808, Proceedings of Epac 88, Rome, Italy.
European Organization for Nuclear Research Cern, Jul. 27, 2000, pp. 1-352.
Johnstone, Koscielniak, "Tune-Stabilized Linear-Field FFAG for Carbon Therapy", Journal, Jun. 26, 2006,Jun. 30, 2006, XP002551807, Proceedings of Epac 2006, Edinburgh, Scotland, UK.
Kalnins, "The use of electric multiple lenses for bending and focusing polar molecules, with application to the design of a rotational-state separator", Journal, May 17, 2003,May 21, 2003, pp. 2951-2953, XP002554356, Proceeding of Pac 2003, Portland, Oregon, USA.
Kim, "50 MeV Proton Beam Test Facility for Low Flux Beam Utilization Studies of PEFP", Journal, Oct. 31, 2005, pp. 441-443, XP002568008, Proceedings of Apac 2004, Pohang, Korea.
Lapostolle, "Introduction a la theorie des accelerateurs lineaires", Book, Jul. 10, 1987, pp. 4-5, XP002554354, Cern Yellow Book Cern, Geneva, Switzerland.
Li, "A thin Beryllium Injection Window for CESR-C", Book, May 12, 2003, pp. 2264-2266, XP002568010, vol. 4, PAC03, Portland, Oregon, USA.
Noda, "Slow beam extraction by a transverse RF field with AM and FM", Journal, May 21, 1996, pp. 269-277, vol. A374, XP002552289, Nuclear Instruments and Methods in Physics Research A, Eslevier, Amsterdam, NL.
Noda, "Performance of a respiration-gated beam control system for patient treatment", Journal, Jun. 10, 1996,Jun. 14, 1996, pp. 2656-2658, XP002552290, Proceedings Epac 96, Barcelona, Spain.
Peters, "Negative ion sources for high energy accelerators", Journal, Feb. 1, 2000, pp. 1069-1074, XP012037926, vol. 71—No. 2,Review of Scientific Instruments, Melville, NY, USA.
Pohlit, "Optimization of Cancer Treatment with Accelerator Produced Radiations", Journal, Jun. 22, 1998, pp. 192-194, XP002552855, Proceedings EPAC 98, Stockholm, Sweden.
Proceeding of 2004 Cyclotron Conference, Oct. 18, 2004, pp. 246-428.
Proceedings of Cyclotron 2004 Conference, Oct. 18, 2004, pp. 243-245 (Presentation Material pp. 1-30).
Proceedings of EPAC 2006, Jun. 30, 2006, pp. 2290-2292.
Proceeding of 2005 Particle Accelerator Conference, May 16, 2005, pp. 261-265.
Saito, "RF Accelerating System for Compact Ion Synchrotron", Journal, Jun. 18, 2001, pp. 966-968, XP002568009, Proceeding of 2001 Pac, Chicago, USA.
Suda, "Medical Application of the Positron Emitter Beam at HIMAC", Journal, Jun. 26, 2000, Jun. 30, 2000, pp. 2554-2556, XP002553046, Proceedings of EPAC 2000, Vienna, Austria.
Tanigaki, "Construction of FFAG Accelerators in KURRI for ADS Study", May 16, 2005,May 20, 2005, pp. 350-352, XP002551809, Proceedings of 2005 Particle Accelerator Conference, Knoxville, Tennessee, USA.
Trbojevic, "Design of a Non-Scaling FFAG Accelerator for Proton Therapy", Journal, Oct. 18, 2004,Oct. 22, 2004, pp. 246-248, XP002551805, Proceedings of 2004 Cyclotron Conference, Tokyo, Japan.
Winkler, "Charge Exchange Extraction at the Experimental Storage Ring ESR at GSI", Journal, Jun. 22, 1998, p. 559-561, XP002552287, Proceedings of Epac 98, Stockholm, Sweden.

\* cited by examiner

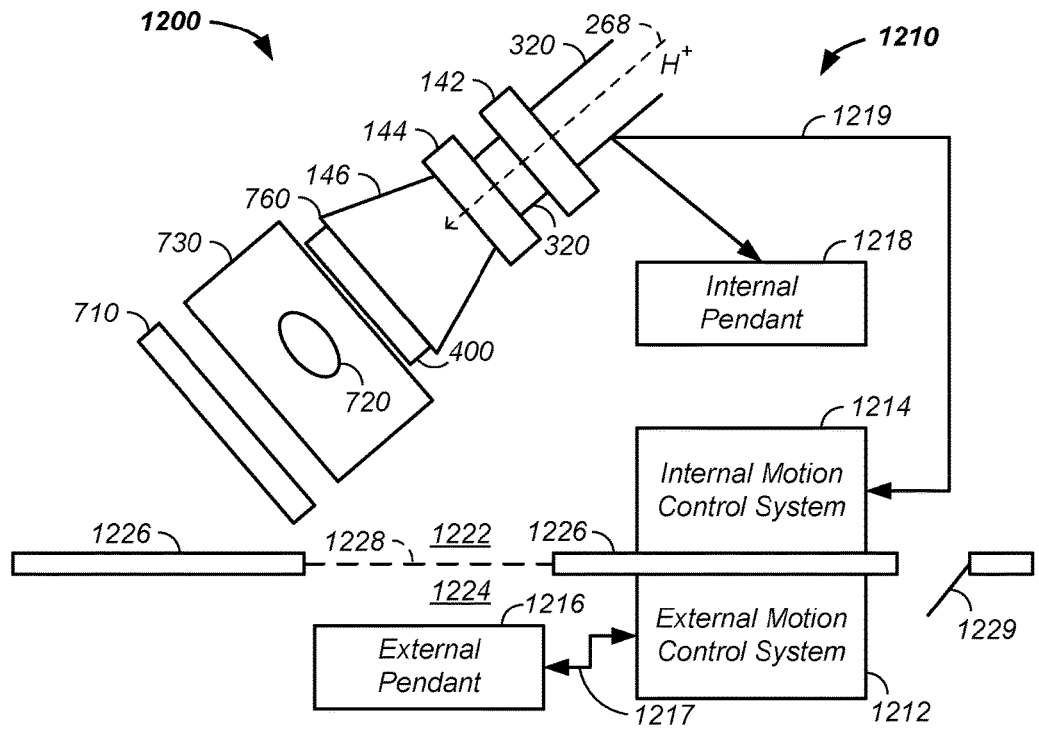
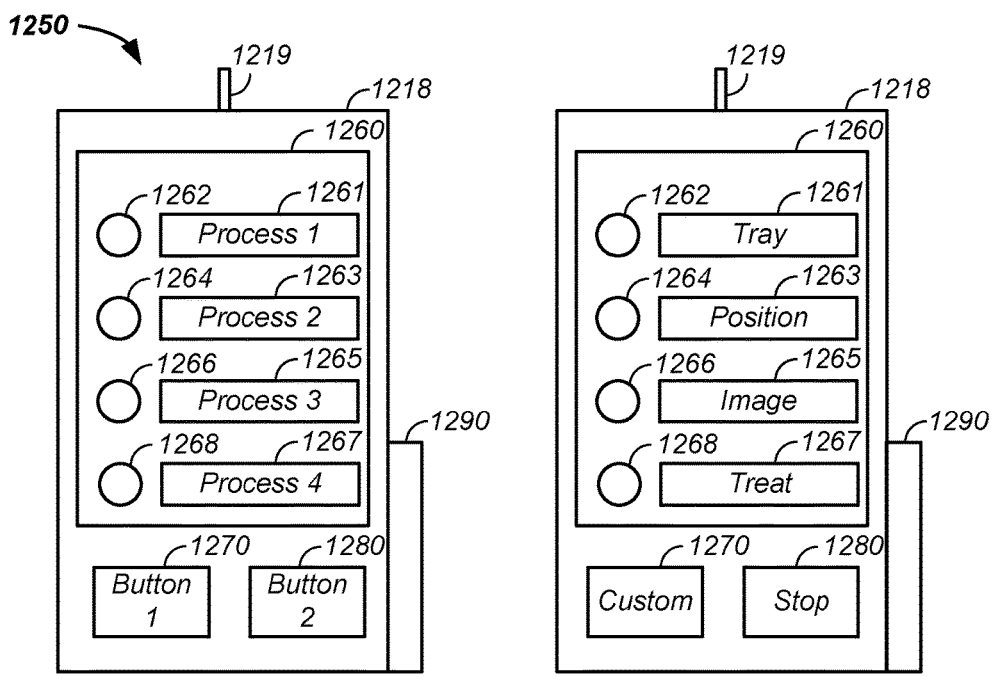

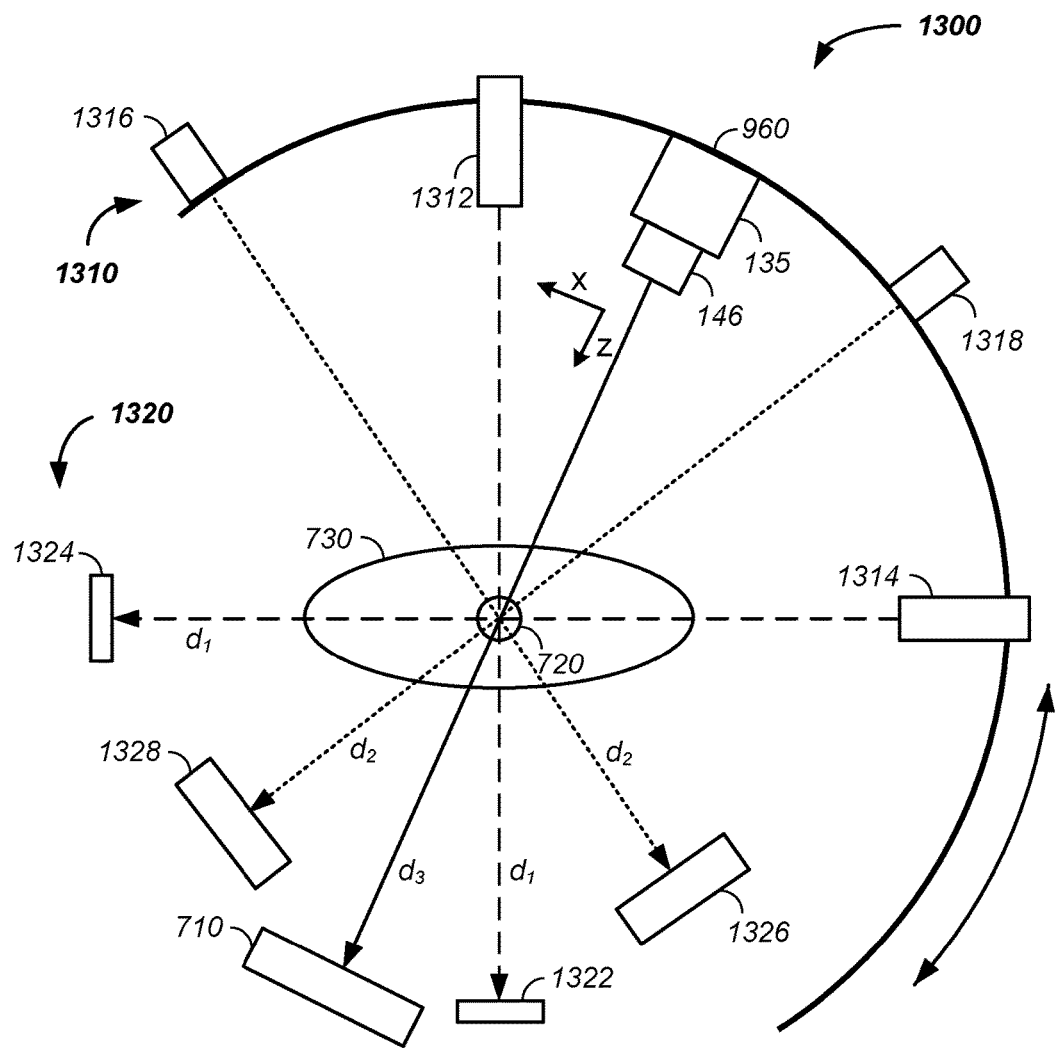
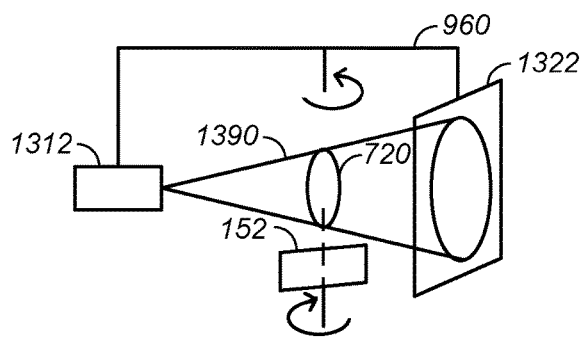
FIG. 13B
FIG. 13C

CHARGED PARTICLE CANCER THERAPY BEAM STATE DETERMINATION APPARATUS AND METHOD OF USE THEREOF

CROSS-REFERENCES TO RELATED APPLICATIONS

This application is a continuation-in-part of U.S. patent application Ser. No. 15/167,617 filed May 27, 2016, which is:

a continuation-in-part of U.S. patent application Ser. No. 15/152,479 filed May 11, 2016, which:

is a continuation-in-part of U.S. patent application Ser. No. 14/216,788 filed Mar. 17, 2014, which is a continuation-in-part of U.S. patent application Ser. No. 13/087,096 filed Apr. 14, 2011, which claims benefit of U.S. provisional patent application No. 61/324,776 filed Apr. 16, 2010; and is a continuation-in-part of U.S. patent application Ser. No. 13/788,890 filed Mar. 7, 2013;

is a continuation-in-part of U.S. patent application Ser. No. 14/952,817 filed Nov. 25, 2015, which is a continuation-in-part of U.S. patent application Ser. No. 14/293,861 filed Jun. 2, 2014, which is a continuation-in-part of U.S. patent application Ser. No. 12/985,039 filed Jan. 5, 2011, which claims the benefit of U.S. provisional patent application No. 61/324,776, filed Apr. 16, 2010;

is a continuation-in-part of U.S. patent application Ser. No. 14/860,577 filed Sep. 21, 2015, which is a continuation of U.S. patent application Ser. No. 14/223,289 filed Mar. 24, 2014, which is a continuation-in-part of U.S. patent application Ser. No. 14/216,788 filed Mar. 17, 2014, which is a continuation-in-part of U.S. patent application Ser. No. 12/985,039 filed Jan. 5, 2011, which claims the benefit of U.S. provisional patent application No. 61/324,776, filed Apr. 16, 2010; and is a continuation-in-part U.S. patent application Ser. No. 15/073,471 filed Mar. 17, 2016, which claims benefit of U.S. provisional patent application No. 62/304,839 filed Mar. 7, 2016, is a continuation-in-part of U.S. patent application Ser. No. 14/860,577 filed Sep. 21, 2015, which is a continuation of U.S. patent application Ser. No. 14/223,289 filed Mar. 24, 2014, which is a continuation-in-part of U.S. patent application Ser. No. 14/216,788 filed Mar. 17, 2014, which is a continuation-in-part of U.S. patent application Ser. No. 13/572,542 filed Aug. 10, 2012, which is a continuation-in-part of U.S. patent application Ser. No. 12/425,683 filed Apr. 17, 2009, which claims the benefit of U.S. provisional patent application No. 61/055,395 filed May 22, 2008, now U.S. Pat. No. 7,939,809 B2;

all of which are incorporated herein in their entirety by this reference thereto.

BACKGROUND OF THE INVENTION

Field of the Invention

The invention relates generally to patient imaging and/or treatment of solid cancers. More particularly, the invention relates to determining a charged particle beam state proximate the patient, after final beam modification, and prior to entry into the patient.

Discussion of the Prior Art

Cancer Treatment

Proton therapy works by aiming energetic ionizing particles, such as protons accelerated with a particle accelerator, onto a target tumor. These particles damage the DNA of cells, ultimately causing their death. Cancerous cells, because of their high rate of division and their reduced ability to repair damaged DNA, are particularly vulnerable to attack on their DNA.

Patents related to the current invention are summarized here.

Proton Beam Therapy System

F. Cole, et. al. of Loma Linda University Medical Center "Multi-Station Proton Beam Therapy System", U.S. Pat. No. 4,870,287 (Sep. 26, 1989) describe a proton beam therapy system for selectively generating and transporting proton beams from a single proton source and accelerator to a selected treatment room of a plurality of patient treatment rooms.

Imaging

P. Adamee, et. al. "Charged Particle Beam Apparatus and Method for Operating the Same", U.S. Pat. No. 7,274,018 (Sep. 25, 2007) and P. Adamee, et. al. "Charged Particle Beam Apparatus and Method for Operating the Same", U.S. Pat. No. 7,045,781 (May 16, 2006) describe a charged particle beam apparatus configured for serial and/or parallel imaging of an object.

K. Hiramoto, et. al. "Ion Beam Therapy System and its Couch Positioning System", U.S. Pat. No. 7,193,227 (Mar. 20, 2007) describe an ion beam therapy system having an X-ray imaging system moving in conjunction with a rotating gantry.

C. Maurer, et. al. "Apparatus and Method for Registration of Images to Physical Space Using a Weighted Combination of Points and Surfaces", U.S. Pat. No. 6,560,354 (May 6, 2003) described a process of X-ray computed tomography registered to physical measurements taken on the patient's body, where different body parts are given different weights. Weights are used in an iterative registration process to determine a rigid body transformation process, where the transformation function is used to assist surgical or stereotactic procedures.

M. Blair, et. al. "Proton Beam Digital Imaging System", U.S. Pat. No. 5,825,845 (Oct. 20, 1998) describe a proton beam digital imaging system having an X-ray source that is movable into a treatment beam line that can produce an X-ray beam through a region of the body. By comparison of the relative positions of the center of the beam in the patient orientation image and the isocentre in the master prescription image with respect to selected monuments, the amount and direction of movement of the patient to make the best beam center correspond to the target isocentre is determined.

S. Nishihara, et. al. "Therapeutic Apparatus", U.S. Pat. No. 5,039,867 (Aug. 13, 1991) describe a method and apparatus for positioning a therapeutic beam in which a first distance is determined on the basis of a first image, a second distance is determined on the basis of a second image, and the patient is moved to a therapy beam irradiation position on the basis of the first and second distances.

Problem

There exists in the art of charged particle irradiation therapy a need to know and/or control position, direction, energy, intensity, cross-sectional area, and/or shape of the charged particle beam relative to a uniquely shaped tumor in a uniquely shaped patient.

SUMMARY OF THE INVENTION

The invention comprises a monitoring apparatus and method of use thereof for determining a positively charged particle beam state after final beam modification and prior to entry to a patient, such as for tumor therapy or tomographic imaging.

DESCRIPTION OF THE FIGURES

A more complete understanding of the present invention is derived by referring to the detailed description and claims when considered in connection with the Figures, wherein like reference numbers refer to similar items throughout the Figures.

FIG. 12A and FIG. 12B illustrate control of a patient interface system with a pendant and work-flow control system, respectively; FIG. 13B illustrates multiple gantry supported imaging systems, and FIG. 13C illustrates a rotatable cone beam.

Figure 1A:
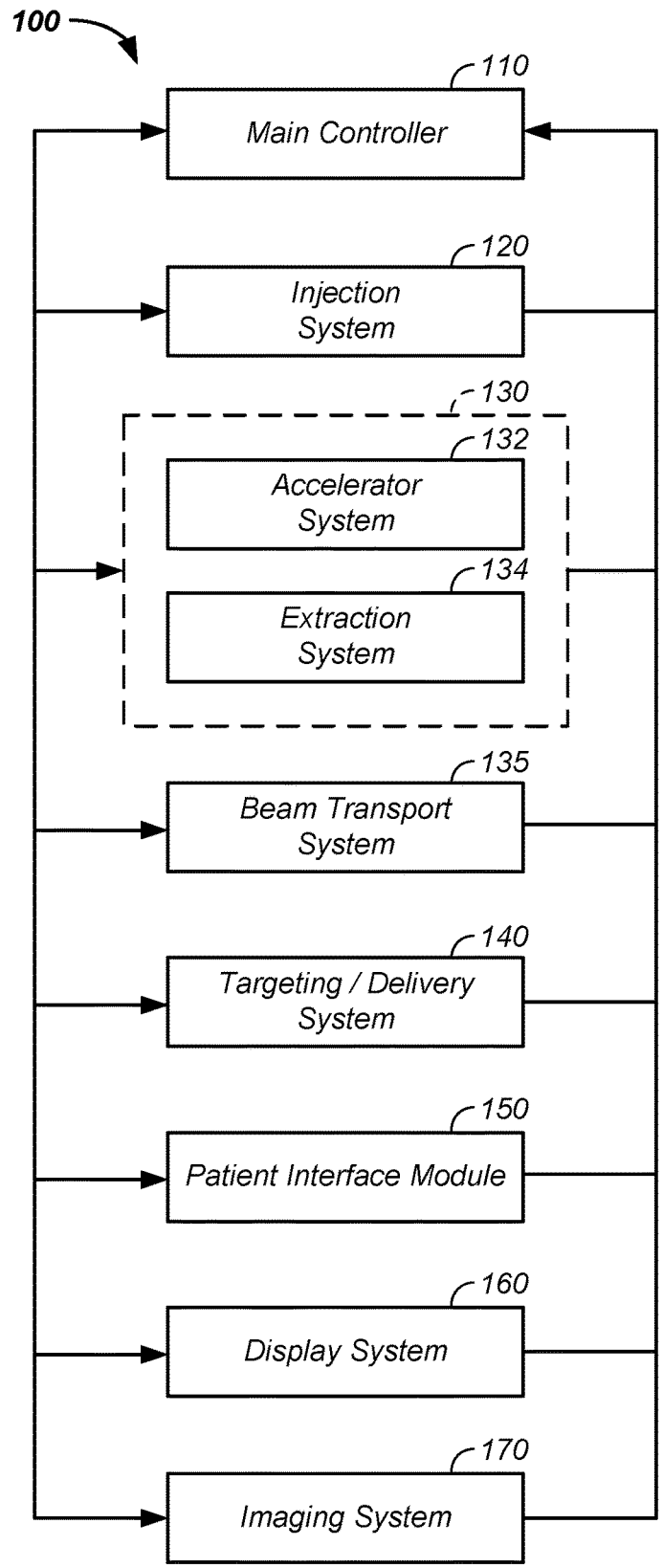
FIG. 1A and FIG. 1B illustrate component connections of a charged particle beam therapy system.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention relates generally to monitoring a charged particle beam state.

In one embodiment, a state of a charged particle beam is monitored and/or checked, such as against a previously established radiation plan, in a position just prior to the beam entering the patient. In one example, the charged particle beam state is measured after a final manipulation of intensity, energy, shape, and/or position, such as via use of an insert, a range filter, a collimator, an aperture, and/or a compensator. In one case, one or more beam crossing elements, sheets, coatings, or layers, configured to emit photons upon passage therethrough by the charged particle beam, are positioned between the final manipulation apparatus, such as the insert, and prior to entry into the patient.

In another embodiment, a patient specific tray insert is inserted into a tray frame to form a beam control tray assembly, the beam control tray assembly is inserted into a slot of a tray receiver assembly, and the tray assembly is positioned relative to a gantry nozzle. Optionally, multiple tray inserts, each used to control a beam state parameter, are inserted into slots of the tray receiver assembly. The beam control tray assembling includes an identifier, such as an electromechanical identifier, of the particular insert type, which is communicated to a main controller, such as via the tray receiver assembly. Optionally and preferably, a hand control pendant is used in loading and/or positioning the tray receiver assembly.

In another embodiment, a gantry positions both: (1) a section of a beam transport system, such as a terminal section, used to transport and direct positively charged particles to a tumor and (2) at least one imaging system. In one case, the imaging system is orientated on a same axis as the positively charged particle, such as at a different time through rotation of the gantry. In another case, the imaging system uses at least two crossing beamlines, each beamline coupled to a respective detector, to yield multiple views of the patient. In another case, one or more imaging subsystem yields a two-dimensional image of the patient, such as for position confirmation and/or as part of a set of images used to develop a three-dimensional image of the patient.

In still another embodiment, multiple linked control stations are used to control position of elements of a beam transport system, nozzle, and/or patient specific beam shaping element relative to a dynamically controlled patient position and/or an imaging surface, element, or system.

In yet another embodiment, a tomography system is optionally used in combination with a charged particle cancer therapy system. Optionally and preferably, a common injector, accelerator, and beam transport system is used for both charged particle based tomographic imaging and charged particle cancer therapy. In one case, an output nozzle of the beam transport system is positioned with a gantry system while the gantry system and/or a patient support maintains a scintillation plate of the tomography system on the opposite side of the patient from the output nozzle.

In another example, a charged particle state determination system, of a cancer therapy system or tomographic imaging system, uses one or more coated layers in conjunction with a scintillation detector or a tomographic imaging system at time of tumor and surrounding tissue sample mapping and/or at time of tumor treatment, such as to determine an input vector of the charged particle beam into a patient and/or an output vector of the charged particle beam from the patient.

In another example, the charged particle tomography apparatus is used in combination with a charged particle cancer therapy system. For example, tomographic imaging of a cancerous tumor is performed using charged particles generated with an injector, accelerator, and guided with a delivery system. The cancer therapy system uses the same injector, accelerator, and guided delivery system in delivering charged particles to the cancerous tumor. For example, the tomography apparatus and cancer therapy system use a common raster beam method and apparatus for treatment of solid cancers. More particularly, the invention comprises a multi-axis and/or multi-field raster beam charged particle accelerator used in: (1) tomography and (2) cancer therapy. Optionally, the system independently controls patient translation position, patient rotation position, two-dimensional beam trajectory, delivered radiation beam energy, delivered radiation beam intensity, beam velocity, timing of charged particle delivery, and/or distribution of radiation striking healthy tissue. The system operates in conjunction with a negative ion beam source, synchrotron, patient positioning, imaging, and/or targeting method and apparatus to deliver an effective and uniform dose of radiation to a tumor while distributing radiation striking healthy tissue.

In another embodiment, a treatment delivery control system (TDCS) or main controller is used to control multiple aspects of the cancer therapy system, including one or more of: an imaging system, such as a CT or PET; a positioner, such as a couch or patient interface module; an injector or injection system; a radio-frequency quadrupole system; a ring accelerator or synchrotron; an extraction system; an irradiation plan; and a display system. The TDCS is preferably a control system for automated cancer therapy once the patient is positioned. The TDCS integrates output of one or more of the below described cancer therapy system elements with inputs of one or more of the below described cancer therapy system elements. More generally, the TDCS controls or manages input and/or output of imaging, an irradiation plan, and charged particle delivery.

In yet another embodiment, one or more trays are inserted into the positively charged particle beam path, such as at or near the exit port of a gantry nozzle in close proximity to the patient. Each tray holds an insert, such as a patient specific insert for controlling the energy, focus depth, and/or shape of the charged particle beam. Examples of inserts include a range shifter, a compensator, an aperture, a ridge filter, and a blank. Optionally and preferably, each tray communicates a held and positioned insert to a main controller of the charged particle cancer therapy system. The trays optionally hold one or more of the imaging sheets configured to emit light upon transmission of the charged particle beam through a corresponding localized position of the one or more imaging sheets.

Charged Particle Beam Therapy

Throughout this document, a charged particle beam therapy system, such as a proton beam, hydrogen ion beam, or carbon ion beam, is described. Herein, the charged particle beam therapy system is described using a proton beam. However, the aspects taught and described in terms of a proton beam are not intended to be limiting to that of a proton beam and are illustrative of a charged particle beam system, a positively charged beam system, and/or a multiply charged particle beam system, such as $C^{4+}$ or $C^{6+}$. Any of the techniques described herein are equally applicable to any charged particle beam system.

Referring now to FIG. 1A, a charged particle beam system 100 is illustrated. The charged particle beam preferably comprises a number of subsystems including any of: a main controller 110; an injection system 120; a synchrotron 130 that typically includes: (1) an accelerator system 132 and (2) an internal or connected extraction system 134; a beam transport system 135; a scanning/targeting/delivery system 140; a patient interface module 150; a display system 160; and/or an imaging system 170.

An exemplary method of use of the charged particle beam system 100 is provided. The main controller 110 controls one or more of the subsystems to accurately and precisely deliver protons to a tumor of a patient. For example, the main controller 110 obtains an image, such as a portion of a body and/or of a tumor, from the imaging system 170. The main controller 110 also obtains position and/or timing information from the patient interface module 150. The main controller 110 optionally controls the injection system 120 to inject a proton into a synchrotron 130. The synchrotron typically contains at least an accelerator system 132 and an extraction system 134. The main controller 110 preferably controls the proton beam within the accelerator system, such as by controlling speed, trajectory, and timing of the proton beam. The main controller then controls extraction of a proton beam from the accelerator through the extraction system 134. For example, the controller controls timing, energy, and/or intensity of the extracted beam. The controller 110 also preferably controls targeting of the proton beam through the scanning/targeting/delivery system 140 to the patient interface module 150. One or more components of the patient interface module 150, such as translational and rotational position of the patient, are preferably controlled by the main controller 110. Further, display elements of the display system 160 are preferably controlled via the main controller 110. Displays, such as display screens, are typically provided to one or more operators and/or to one or more patients. In one embodiment, the main controller 110 times the delivery of the proton beam from all systems, such that protons are delivered in an optimal therapeutic manner to the tumor of the patient.

Herein, the main controller 110 refers to a single system controlling the charged particle beam system 100, to a single controller controlling a plurality of subsystems controlling the charged particle beam system 100, or to a plurality of individual controllers controlling one or more sub-systems of the charged particle beam system 100.

EXAMPLE I

Charged Particle Cancer Therapy System Control

Figure 1B:
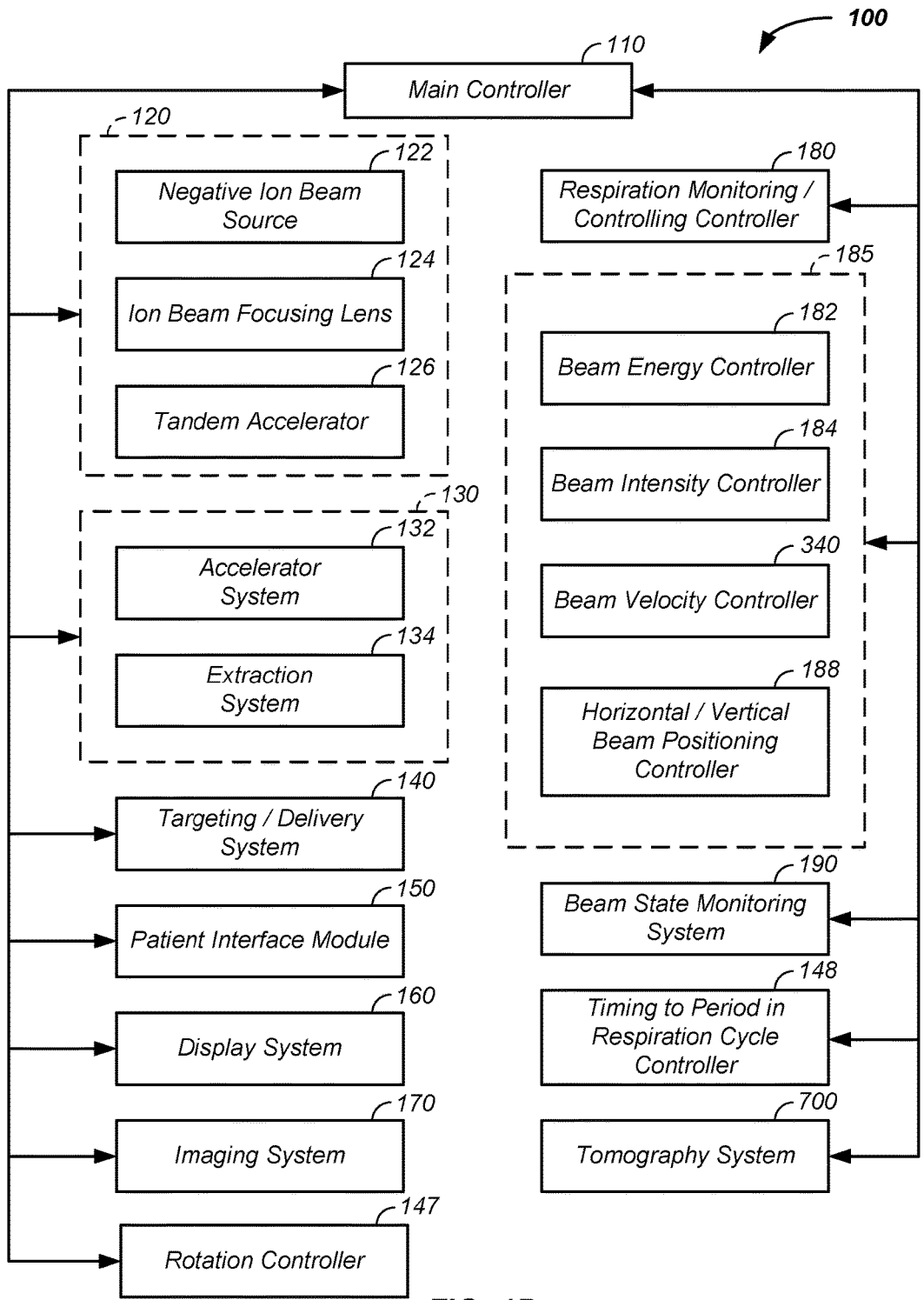

Referring now to FIG. 1B, an example of a charged particle cancer therapy system 100 is provided. A main controller receives input from one, two, three, or four of a respiration monitoring and/or controlling controller 180, a beam controller 185, a rotation controller 147, and/or a timing to a time period in a respiration cycle controller 148. The beam controller 185 preferably includes one or more or a beam energy controller 182, the beam intensity controller 340, a beam velocity controller 186, and/or a horizontal/vertical beam positioning controller 188. The main controller 110 controls any element of the injection system 120; the synchrotron 130; the scanning/targeting/delivery system 140; the patient interface module 150; the display system 160; and/or the imaging system 170. For example, the respiration monitoring/controlling controller 180 controls any element or method associated with the respiration of the patient; the beam controller 185 controls any of the elements controlling acceleration and/or extraction of the charged particle beam; the rotation controller 147 controls any element associated with rotation of the patient 830 or gantry; and the timing to a period in respiration cycle controller 148 controls any aspects affecting delivery time of the charged particle beam to the patient. As a further example, the beam controller 185 optionally controls any magnetic and/or electric field about any magnet in the charged particle cancer therapy system 100. One or more beam state sensors 190 sense position, direction, intensity, and/or energy of the charged particles at one or more positions in the charged particle beam path. A tomography system 700, described infra, is optionally used to monitor intensity and/or position of the charged particle beam.

Figure 2:
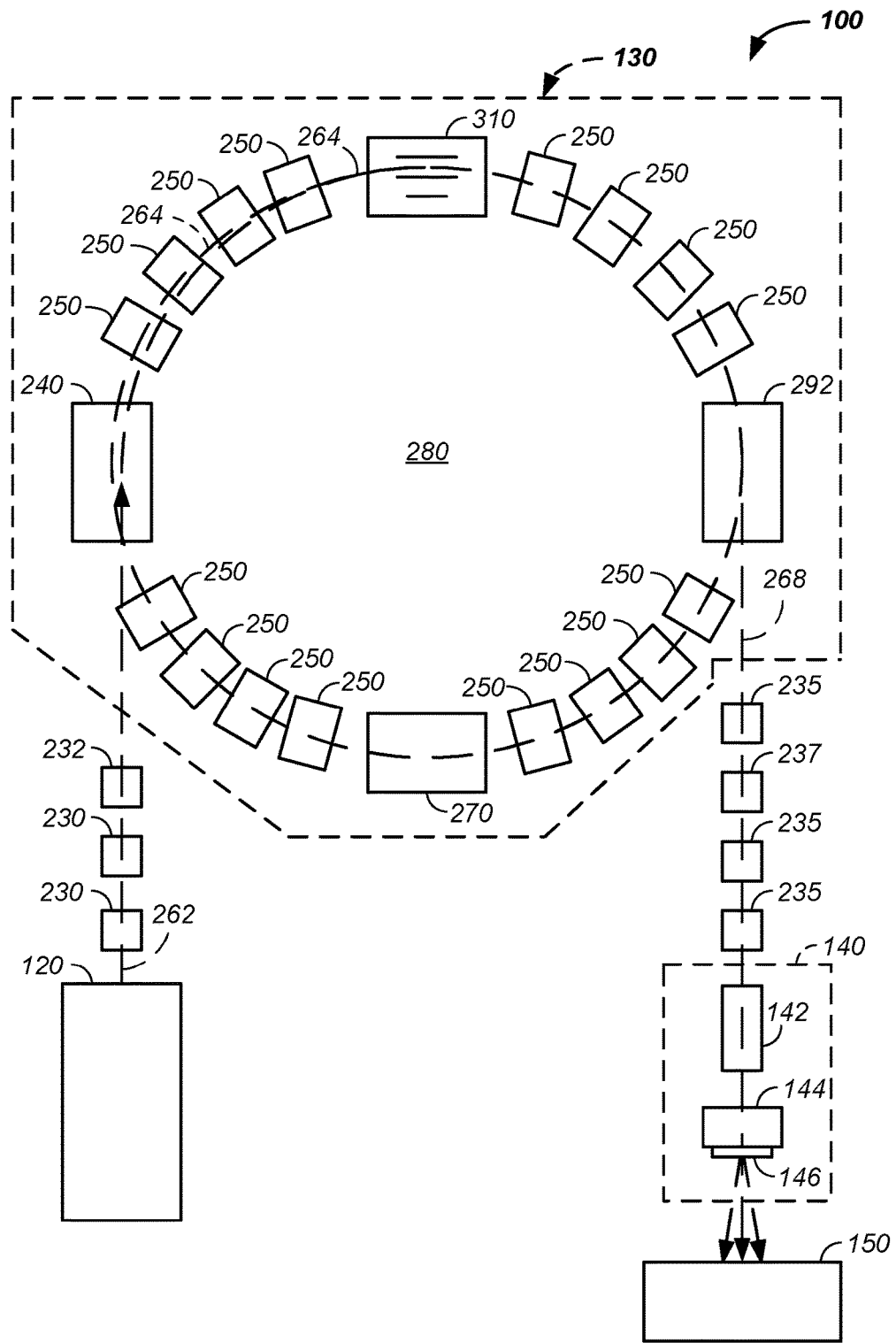
FIG. 2 illustrates a charged particle therapy system.

Referring now to FIG. 2, an illustrative exemplary embodiment of one version of the charged particle beam system 100 is provided. The number, position, and described type of components is illustrative and non-limiting in nature. In the illustrated embodiment, the injection system 120 or ion source or charged particle beam source generates protons. The injection system 120 optionally includes one or more of: a negative ion beam source, an ion beam focusing lens, and a tandem accelerator. The protons are delivered into a vacuum tube that runs into, through, and out of the synchrotron. The generated protons are delivered along an initial path 262. Focusing magnets 230, such as quadrupole magnets or injection quadrupole magnets, are used to focus the proton beam path. A quadrupole magnet is a focusing magnet. An injector bending magnet 232 bends the proton beam toward a plane of the synchrotron 130. The focused protons having an initial energy are introduced into an injector magnet 240, which is preferably an injection Lamberson magnet. Typically, the initial beam path 262 is along an axis off of, such as above, a circulating plane of the synchrotron 130. The injector bending magnet 232 and injector magnet 240 combine to move the protons into the synchrotron 130. Main bending magnets, dipole magnets, turning magnets, or circulating magnets 250 are used to turn the protons along a circulating beam path 264. A dipole magnet is a bending magnet. The main bending magnets 250 bend the initial beam path 262 into a circulating beam path 264. In this example, the main bending magnets 250 or circulating magnets are represented as four sets of four magnets to maintain the circulating beam path 264 into a stable circulating beam path. However, any number of magnets or sets of magnets are optionally used to move the protons around a single orbit in the circulation process. The protons pass through an accelerator 270. The accelerator accelerates the protons in the circulating beam path 264. As the protons are accelerated, the fields applied by the magnets are increased. Particularly, the speed of the protons achieved by the accelerator 270 are synchronized with magnetic fields of the main bending magnets 250 or circulating magnets to maintain stable circulation of the protons about a central point or region 280 of the synchrotron. At separate points in time the accelerator 270/main bending magnet 250 combination is used to accelerate and/or decelerate the circulating protons while maintaining the protons in the circulating path or orbit. An extraction element of an inflector/deflector system is used in combination with a Lamberson extraction magnet 292 to remove protons from their circulating beam path 264 within the synchrotron 130. One example of a deflector component is a Lamberson magnet. Typically the deflector moves the protons from the circulating plane to an axis off of the circulating plane, such as above the circulating plane. Extracted protons are preferably directed and/or focused using an extraction bending magnet 237 and extraction focusing magnets 235, such as quadrupole magnets along a positively charged particle beam transport path 268 in a beam transport system 135, such as a beam path or proton beam path, into the scanning/targeting/delivery system 140. Two components of a scanning system 140 or targeting system typically include a first axis control 142, such as a vertical control, and a second axis control 144, such as a horizontal control. In one embodiment, the first axis control 142 allows for about 100 mm of vertical or y-axis scanning of the proton beam 268 and the second axis control 144 allows for about 700 mm of horizontal or x-axis scanning of the proton beam 268. A nozzle system 146 is used for imaging the proton beam, for defining shape of the proton beam, and/or as a vacuum barrier between the low pressure beam path of the synchrotron and the atmosphere. Protons are delivered with control to the patient interface module 150 and to a tumor of a patient. All of the above listed elements are optional and may be used in various permutations and combinations.

Proton Beam Extraction

Figure 3:
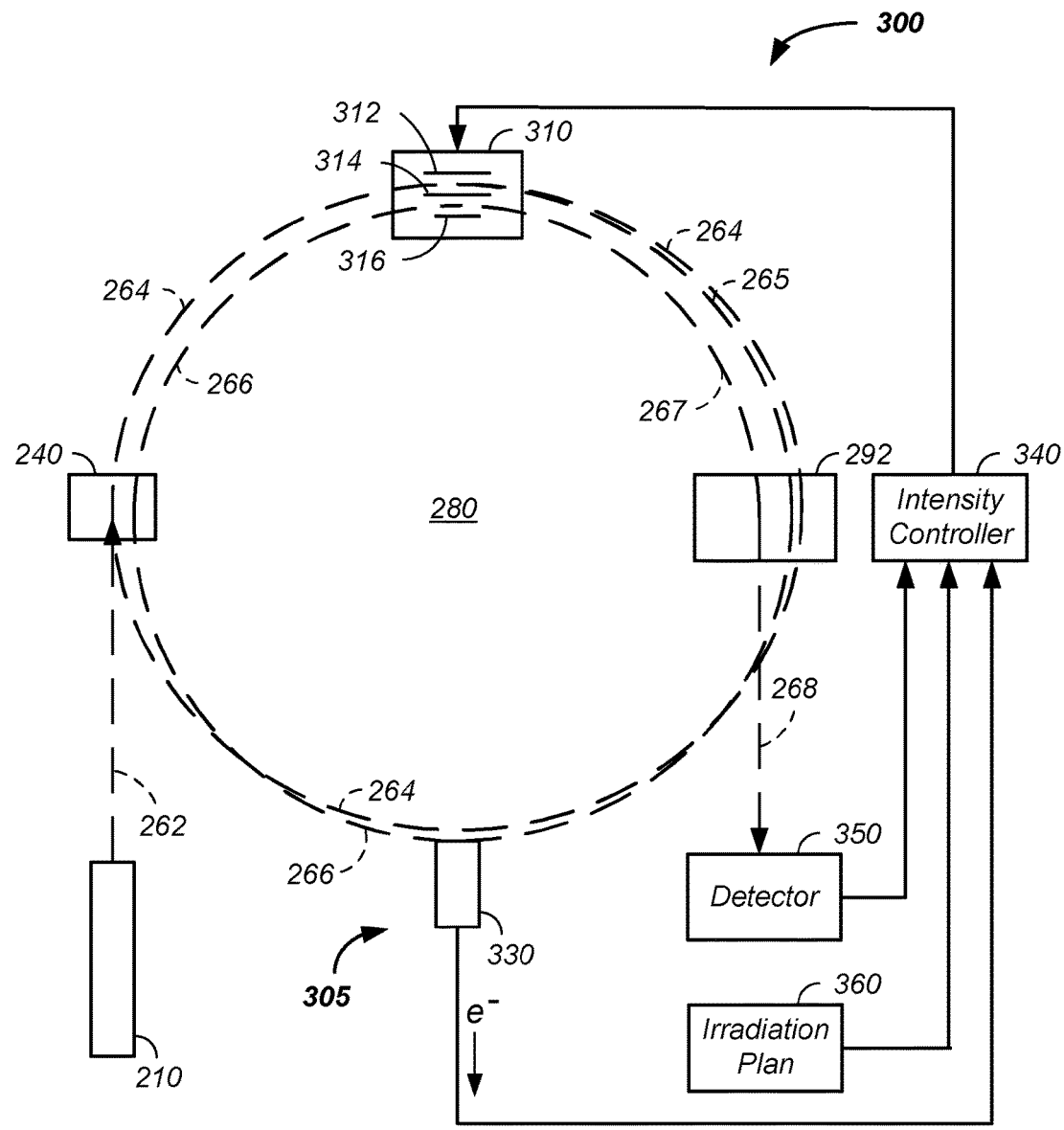
FIG. 3 illustrates a method of multi-axis charged particle beam irradiation control.

Referring now to FIG. 3, both: (1) an exemplary proton beam extraction system 300 from the synchrotron 130 and (2) a charged particle beam intensity control system 305 are illustrated. For clarity, FIG. 3 removes elements represented in FIG. 2, such as the turning magnets, which allows for greater clarity of presentation of the proton beam path as a function of time. Generally, protons are extracted from the synchrotron 130 by slowing the protons. As described, supra, the protons were initially accelerated in a circulating path, which is maintained with a plurality of main bending magnets 250. The circulating path is referred to herein as an original central beamline 264. The protons repeatedly cycle around a central point in the synchrotron 280. The proton path traverses through a radio frequency (RF) cavity system 310. To initiate extraction, an RF field is applied across a first blade 312 and a second blade 314, in the RF cavity system 310. The first blade 312 and second blade 314 are referred to herein as a first pair of blades.

In the proton extraction process, an RF voltage is applied across the first pair of blades, where the first blade 312 of the first pair of blades is on one side of the circulating proton beam path 264 and the second blade 314 of the first pair of blades is on an opposite side of the circulating proton beam path 264. The applied RF field applies energy to the circulating charged-particle beam. The applied RF field alters the orbiting or circulating beam path slightly of the protons from the original central beamline 264 to an altered circulating beam path 265. Upon a second pass of the protons through the RF cavity system, the RF field further moves the protons off of the original proton beamline 264. For example, if the original beamline is considered as a circular path, then the altered beamline is slightly elliptical. The frequency of the applied RF field is timed to apply outward or inward movement to a given band of protons circulating in the synchrotron accelerator. Orbits of the protons are slightly more off axis compared to the original circulating beam path 264. Successive passes of the protons through the RF cavity system are forced further and further from the original central beamline 264 by altering the direction and/or intensity of the RF field with each successive pass of the proton beam through the RF field. Timing of application of the RF field and/or frequency of the RF field is related to the circulating charged particles circulation pathlength in the synchrotron 130 and the velocity of the charged particles so that the applied RF field has a period, with a peak-to-peak time period, equal to a period of time of beam circulation in the synchrotron 130 about the center 280 or an integer multiple of the time period of beam circulation about the center 280 of the synchrotron 130. Alternatively, the time period of beam circulation about the center 280 of the synchrotron 130 is an integer multiple of the RF period time. The RF period is optionally used to calculated the velocity of the charged particles, which relates directly to the energy of the circulating charged particles.

The RF voltage is frequency modulated at a frequency about equal to the period of one proton cycling around the synchrotron for one revolution or at a frequency than is an integral multiplier of the period of one proton cycling about the synchrotron. The applied RF frequency modulated voltage excites a betatron oscillation. For example, the oscillation is a sine wave motion of the protons. The process of timing the RF field to a given proton beam within the RF cavity system is repeated thousands of times with each successive pass of the protons being moved approximately one micrometer further off of the original central beamline 264. For clarity, the approximately 1000 changing beam paths with each successive path of a given band of protons through the RF field are illustrated as the altered beam path 265. The RF time period is process is known, thus energy of the charged particles at time of hitting the extraction material or material 330, described infra, is known.

With a sufficient sine wave betatron amplitude, the altered circulating beam path 265 touches and/or traverses a material 330, such as a foil or a sheet of foil. The foil is preferably a lightweight material, such as beryllium, a lithium hydride, a carbon sheet, or a material having low nuclear charge components. Herein, a material of low nuclear charge is a material composed of atoms consisting essentially of atoms having six or fewer protons. The foil is preferably about 10 to 150 microns thick, is more preferably about 30 to 100 microns thick, and is still more preferably about 40 to 60 microns thick. In one example, the foil is beryllium with a thickness of about 50 microns. When the protons traverse through the foil, energy of the protons is lost and the speed of the protons is reduced. Typically, a current is also generated, described infra. Protons moving at the slower speed travel in the synchrotron with a reduced radius of curvature 266 compared to either the original central beamline 264 or the altered circulating path 265. The reduced radius of curvature 266 path is also referred to herein as a path having a smaller diameter of trajectory or a path having protons with reduced energy. The reduced radius of curvature 266 is typically about two millimeters less than a radius of curvature of the last pass of the protons along the altered proton beam path 265.

The thickness of the material 330 is optionally adjusted to create a change in the radius of curvature, such as about ½, 1, 2, 3, or 4 mm less than the last pass of the protons 265 or original radius of curvature 264. The reduction in velocity of the charged particles transmitting through the material 330 is calculable, such as by using the pathlength of the betatron oscillating charged particle beam through the material 330 and/or using the density of the material 330. Protons moving with the smaller radius of curvature travel between a second pair of blades. In one case, the second pair of blades is physically distinct and/or is separated from the first pair of blades. In a second case, one of the first pair of blades is also a member of the second pair of blades. For example, the second pair of blades is the second blade 314 and a third blade 316 in the RF cavity system 310. A high voltage DC signal, such as about 1 to 5 kV, is then applied across the second pair of blades, which directs the protons out of the synchrotron through an extraction magnet 292, such as a Lamberson extraction magnet, into a transport path 268.

Control of acceleration of the charged particle beam path in the synchrotron with the accelerator and/or applied fields of the turning magnets in combination with the above described extraction system allows for control of the intensity of the extracted proton beam, where intensity is a proton flux per unit time or the number of protons extracted as a function of time. For example, when a current is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In another embodiment, instead of moving the charged particles to the material 330, the material 330 is mechanically moved to the circulating charged particles. Particularly, the material 330 is mechanically or electromechanically translated into the path of the circulating charged particles to induce the extraction process, described supra. In this case, the velocity or energy of the circulating charged particle beam is calculable using the pathlength of the beam path about the center 280 of the synchrotron 130 and from the force applied by the bending magnets 250.

In either case, because the extraction system does not depend on any change in magnetic field properties, it allows the synchrotron to continue to operate in acceleration or deceleration mode during the extraction process. Stated differently, the extraction process does not interfere with synchrotron acceleration. In stark contrast, traditional extraction systems introduce a new magnetic field, such as via a hexapole, during the extraction process. More particularly, traditional synchrotrons have a magnet, such as a hexapole magnet, that is off during an acceleration stage. During the extraction phase, the hexapole magnetic field is introduced to the circulating path of the synchrotron. The introduction of the magnetic field necessitates two distinct modes, an acceleration mode and an extraction mode, which are mutually exclusive in time. The herein described system allows for acceleration and/or deceleration of the proton during the extraction step and tumor treatment without the use of a newly introduced magnetic field, such as by a hexapole magnet.

Charged Particle Beam Intensity Control

Control of applied field, such as a radio-frequency (RF) field, frequency and magnitude in the RF cavity system 310 allows for intensity control of the extracted proton beam, where intensity is extracted proton flux per unit time or the number of protons extracted as a function of time.

Still referring FIG. 3, the intensity control system 305 is further described. In this example, an intensity control feedback loop is added to the extraction system, described supra. When protons in the proton beam hit the material 330 electrons are given off from the material 330 resulting in a current. The resulting current is converted to a voltage and is used as part of an ion beam intensity monitoring system or as part of an ion beam feedback loop for controlling beam intensity. The voltage is optionally measured and sent to the main controller 110 or to an intensity controller subsystem 340, which is preferably in communication or under the direction of the main controller 110. More particularly, when protons in the charged particle beam path pass through the material 330, some of the protons lose a small fraction of their energy, such as about one-tenth of a percent, which results in a secondary electron. That is, protons in the charged particle beam push some electrons when passing through material 330 giving the electrons enough energy to cause secondary emission. The resulting electron flow results in a current or signal that is proportional to the number of protons going through the target or extraction material 330. The resulting current is preferably converted to voltage and amplified. The resulting signal is referred to as a measured intensity signal.

The amplified signal or measured intensity signal resulting from the protons passing through the material 330 is optionally used in monitoring the intensity of the extracted protons and is preferably used in controlling the intensity of the extracted protons. For example, the measured intensity signal is compared to a goal signal, which is predetermined in an irradiation of the tumor plan. The difference between the measured intensity signal and the planned for goal signal is calculated. The difference is used as a control to the RF generator. Hence, the measured flow of current resulting from the protons passing through the material 330 is used as a control in the RF generator to increase or decrease the number of protons undergoing betatron oscillation and striking the material 330. Hence, the voltage determined off of the material 330 is used as a measure of the orbital path and is used as a feedback control to control the RF cavity system.

In one example, the intensity controller subsystem 340 preferably additionally receives input from: (1) a detector 350, which provides a reading of the actual intensity of the proton beam and/or (2) an irradiation plan 360. The irradiation plan provides the desired intensity of the proton beam for each x, y, energy, and/or rotational position of the patient/tumor as a function of time. Thus, the intensity controller 340 receives the desired intensity from the irradiation plan 350, the actual intensity from the detector 350 and/or a measure of intensity from the material 330, and adjusts the amplitude and/or the duration of application of the applied radio-frequency field in the RF cavity system 310 to yield an intensity of the proton beam that matches the desired intensity from the irradiation plan 360.

As described, supra, the protons striking the material 330 is a step in the extraction of the protons from the synchrotron 130. Hence, the measured intensity signal is used to change the number of protons per unit time being extracted, which is referred to as intensity of the proton beam. The intensity of the proton beam is thus under algorithm control. Further, the intensity of the proton beam is controlled separately from the velocity of the protons in the synchrotron 130. Hence, intensity of the protons extracted and the energy of the protons extracted are independently variable. Still further, the intensity of the extracted protons is controllably variable while scanning the charged particles beam in the tumor from one voxel to an adjacent voxel as a separate hexapole and separated time period from acceleration and/or treatment is not required, as described supra.

For example, protons initially move at an equilibrium trajectory in the synchrotron 130. An RF field is used to excite or move the protons into a betatron oscillation. In one case, the frequency of the protons orbit is about 10 MHz. In one example, in about one millisecond or after about 10,000 orbits, the first protons hit an outer edge of the target material 130. The specific frequency is dependent upon the period of the orbit. Upon hitting the material 130, the protons push electrons through the foil to produce a current. The current is converted to voltage and amplified to yield a measured intensity signal. The measured intensity signal is used as a feedback input to control the applied RF magnitude or RF field. An energy beam sensor, described infra, is optionally used as a feedback control to the RF field frequency or RF field of the RF field extraction system 310 to dynamically control, modify, and/or alter the delivered charge particle beam energy, such as in a continuous pencil beam scanning system operating to treat tumor voxels without alternating between an extraction phase and a treatment phase. Preferably, the measured intensity signal is compared to a target signal and a measure of the difference between the measured intensity signal and target signal is used to adjust the applied RF field in the RF cavity system 310 in the extraction system to control the intensity of the protons in the extraction step. Stated again, the signal resulting from the protons striking and/or passing through the material 130 is used as an input in RF field modulation.

An increase in the magnitude of the RF modulation results in protons hitting the foil or material 130 sooner. By increasing the RF, more protons are pushed into the foil, which results in an increased intensity, or more protons per unit time, of protons extracted from the synchrotron 130.

In another example, a detector 350 external to the synchrotron 130 is used to determine the flux of protons extracted from the synchrotron and a signal from the external detector is used to alter the RF field, RF intensity, RF amplitude, and/or RF modulation in the RF cavity system 310. Here the external detector generates an external signal, which is used in a manner similar to the measured intensity signal, described in the preceding paragraphs. Preferably, an algorithm or irradiation plan 360 is used as an input to the intensity controller 340, which controls the RF field modulation by directing the RF signal in the betatron oscillation generation in the RF cavity system 310. The irradiation plan 360 preferably includes the desired intensity of the charged particle beam as a function of time and/or energy of the charged particle beam as a function of time, for each patient rotation position, and/or for each x-, y-position of the charged particle beam.

In yet another example, when a current from material 330 resulting from protons passing through or hitting material is measured beyond a threshold, the RF field modulation in the RF cavity system is terminated or reinitiated to establish a subsequent cycle of proton beam extraction. This process is repeated to yield many cycles of proton beam extraction from the synchrotron accelerator.

In still yet another embodiment, intensity modulation of the extracted proton beam is controlled by the main controller 110. The main controller 110 optionally and/or additionally controls timing of extraction of the charged particle beam and energy of the extracted proton beam.

The benefits of the system include a multi-dimensional scanning system. Particularly, the system allows independence in: (1) energy of the protons extracted and (2) intensity of the protons extracted. That is, energy of the protons extracted is controlled by an energy control system and an intensity control system controls the intensity of the extracted protons. The energy control system and intensity control system are optionally independently controlled. Preferably, the main controller 110 controls the energy control system and the main controller 110 simultaneously controls the intensity control system to yield an extracted proton beam with controlled energy and controlled intensity where the controlled energy and controlled intensity are independently variable and/or continually available as a separate extraction phase and acceleration phase are not required, as described supra. Thus the irradiation spot hitting the tumor is under independent control of:
 time;
 energy;
 intensity;
 x-axis position, where the x-axis represents horizontal movement of the proton beam relative to the patient, and
 y-axis position, where the y-axis represents vertical movement of the proton beam relative to the patient.

In addition, the patient is optionally independently translated and/or rotated relative to a translational axis of the proton beam at the same time.

Beam Transport

The beam transport system 135 is used to move the charged particles from the accelerator to the patient, such as via a nozzle in a gantry, described infra.

Charged Particle Energy

The beam transport system 135 optionally includes means for determining an energy of the charged particles in the charged particle beam. For example, an energy of the charged particle beam is determined via calculation, such as via equation 1, using knowledge of a magnet geometry and applied magnetic field to determine mass and/or energy. Referring now to equation 1, for a known magnet geometry, charge, q, and magnetic field, B, the Larmor radius, $\rho_L$, or magnet bend radius is defined as:

$$\rho_L = \frac{v_\perp}{\Omega_c} = \frac{\sqrt{2Em}}{qB} \qquad (\text{eq. 1})$$

where: $v_\perp$ is the ion velocity perpendicular to the magnetic field, $\Omega_c$ is the cyclotron frequency, q is the charge of the ion, B is the magnetic field, m is the mass of the charge particle, and E is the charged particle energy. Solving for the charged particle energy yields equation 2.

$$E = \frac{(\rho_L qB)^2}{2m} \qquad (\text{eq. 2})$$

Thus, an energy of the charged particle in the charged particle beam in the beam transport system 135 is calculable from the know magnet geometry, known or measured magnetic field, charged particle mass, charged particle charge, and the known magnet bend radius, which is proportional to and/or equivalent to the Larmor radius.

Nozzle

After extraction from the synchrotron 130 and transport of the charged particle beam along the proton beam path 268 in the beam transport system 135, the charged particle beam exits through the nozzle system 146. In one example, the nozzle system includes a nozzle foil covering an end of the nozzle system 146 or a cross-sectional area within the nozzle system forming a vacuum seal. The nozzle system includes a nozzle that expands in x/y-cross-sectional area along the z-axis of the proton beam path 268 to allow the proton beam 268 to be scanned along the x-axis and y-axis by the vertical control element and horizontal control element, respectively. The nozzle foil is preferably mechanically supported by the outer edges of an exit port of the nozzle 146. An example of a nozzle foil is a sheet of about 0.1 inch thick aluminum foil. Generally, the nozzle foil separates atmosphere pressures on the patient side of the nozzle foil from the low pressure region, such as about $10^{-5}$ to $10^{-7}$ torr region, on the synchrotron 130 side of the nozzle foil. The low pressure region is maintained to reduce scattering of the circulating charged particle beam in the synchrotron. Herein, the exit foil of the nozzle is optionally the first sheet 760 of the charged particle beam state determination system 750, described infra.

Charged Particle Control

Referring now to FIG. 4A, FIG. 4B, FIG. 5, FIG. 6A, and FIG. 6B, a charged particle beam control system is described where one or more patient specific beam control assemblies are removably inserted into the charged particle beam path proximate the nozzle of the charged particle cancer therapy system 100, where the patient specific beam control assemblies adjust the beam energy, diameter, cross-sectional shape, focal point, and/or beam state of the charged particle beam to properly couple energy of the charged particle beam to the individual's specific tumor.

Beam Control Tray

Figure 4A:
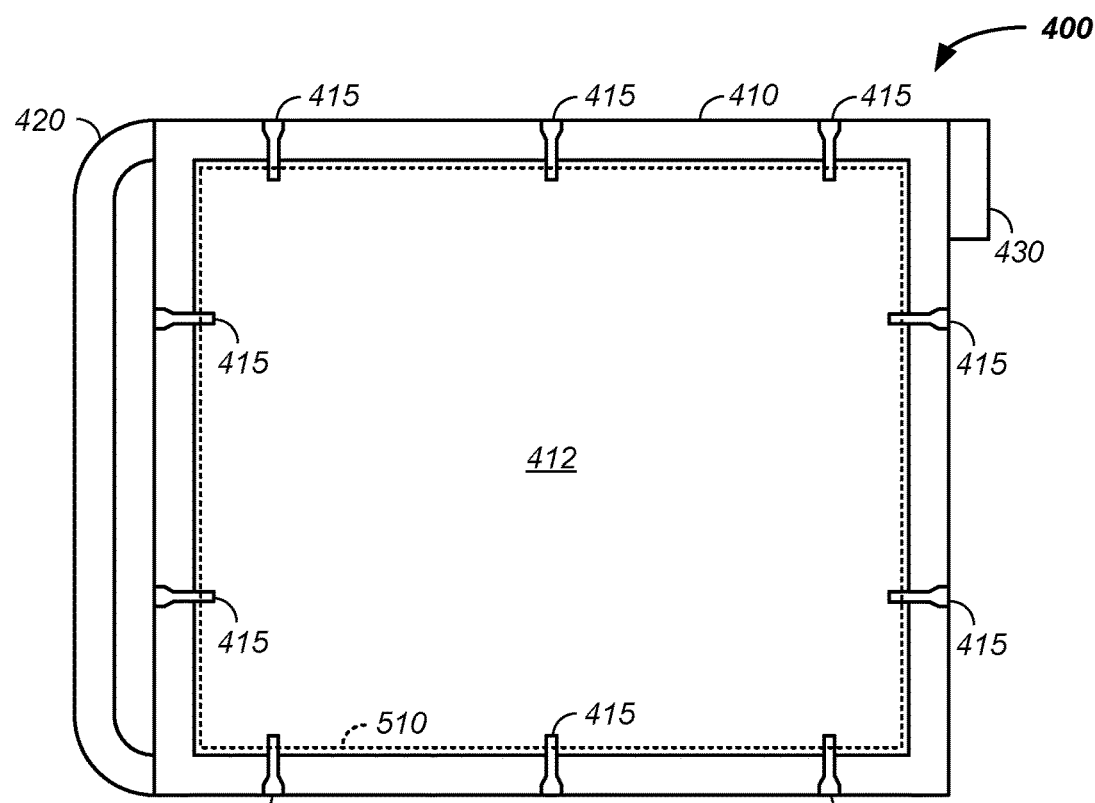
FIG. 4A and FIG. 4B illustrate a top view of a beam control tray and a side view of the beam control tray, respectively.
Figure 4B:
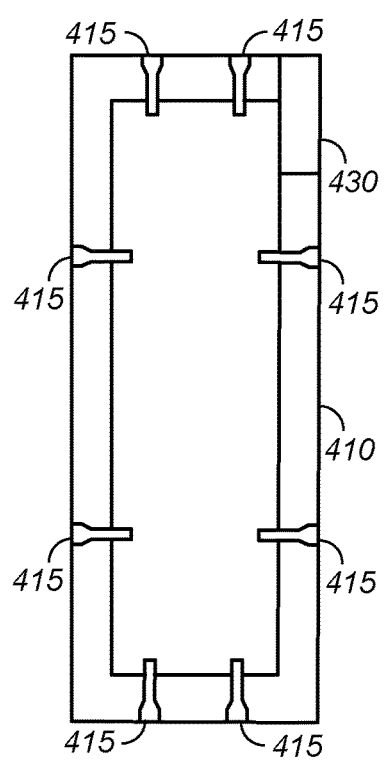

Referring now to FIG. 4A and FIG. 4B, a beam control tray assembly 400 is illustrated in a top view and side view, respectively. The beam control tray assembly 400 optionally comprises any of a tray frame 410, a tray aperture 412, a tray handle 420, a tray connector/communicator 430, and means for holding a patient specific tray insert 510, described infra. Generally, the beam control tray assembly 400 is used to: (1) hold the patient specific tray insert 510 in a rigid location relative to the beam control tray 400, (2) electronically identify the held patient specific tray insert 510 to the main controller 110, and (3) removably insert the patient specific tray insert 510 into an accurate and precise fixed location relative to the charged particle beam, such as the proton beam path 268 at the nozzle of the charged particle cancer therapy system 100.

For clarity of presentation and without loss of generality, the means for holding the patient specific tray insert 510 in the tray frame 410 of the beam control tray assembly 400 is illustrated as a set of recessed set screws 415. However, the means for holding the patient specific tray insert 510 relative to the rest of the beam control tray assembly 400 is optionally any mechanical and/or electromechanical positioning element, such as a latch, clamp, fastener, clip, slide, strap, or the like. Generally, the means for holding the patient specific tray insert 510 in the beam control tray 400 fixes the tray insert and tray frame relative to one another even when rotated along and/or around multiple axes, such as when attached to a charged particle cancer therapy system 100 dynamic gantry nozzle 610 or gantry nozzle, which is an optional element of the nozzle system 146, that moves in three-dimensional space relative to a fixed point in the beamline, proton beam path 268, and/or a given patient position. As illustrated in FIG. 4A and FIG. 4B, the recessed set screws 415 fix the patient specific tray insert 510 into the aperture 412 of the tray frame 410. The tray frame 410 is illustrated as circumferentially surrounding the patient specific tray insert 510, which aids in structural stability of the beam control tray assembly 400. However, generally the tray frame 410 is of any geometry that forms a stable beam control tray assembly 400.

Figure 5:
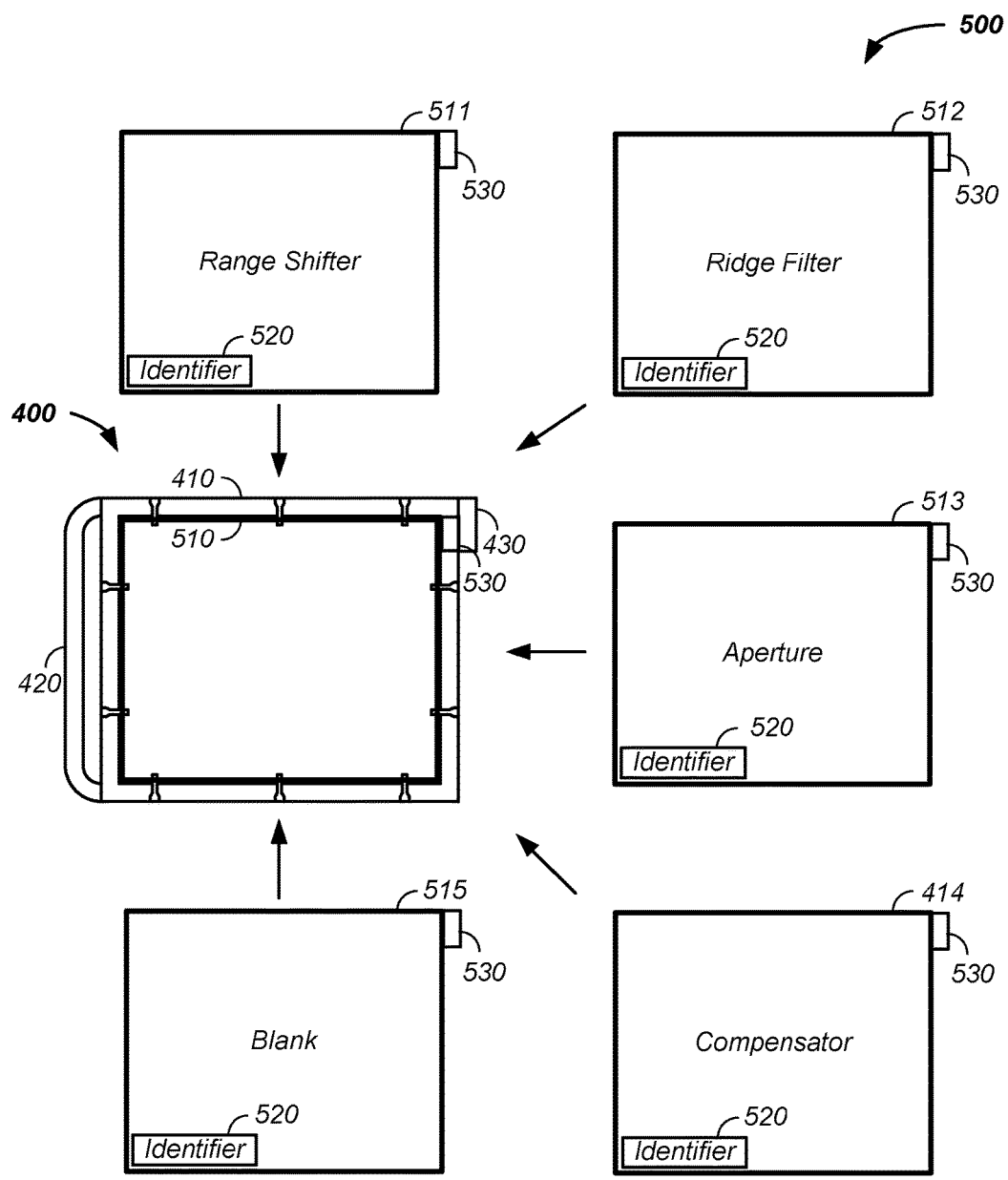
FIG. 5 illustrates patient specific tray inserts for insertion into the beam control tray.
Figure 6A:
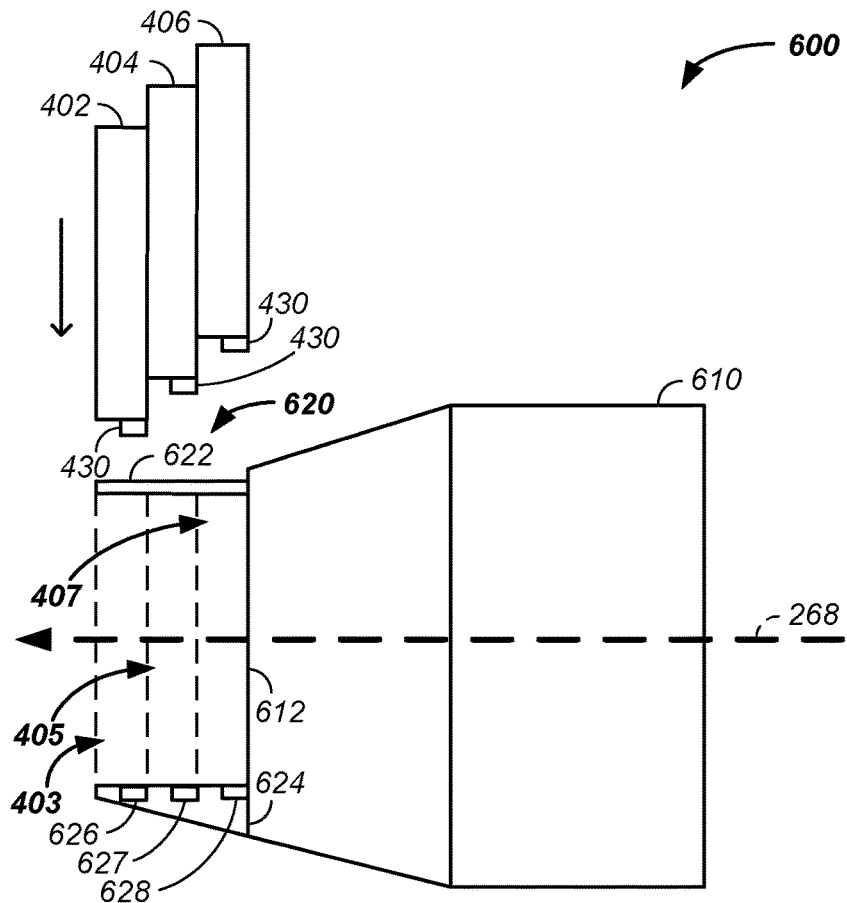
FIG. 6A illustrates insertion of the individualized tray assembly into the beam path and FIG. 6B illustrates retraction of the tray assembly into a nozzle of the charged particle cancer therapy system.

Still referring to FIG. 4A and now referring to FIG. 5 and FIG. 6A, the optional tray handle 420 is used to manually insert/retract the beam control tray assembly 400 into a receiving element of the gantry nozzle or dynamic gantry nozzle 610. While the beam control tray assembly 400 is optionally inserted into the charged particle beam path 268 at any point after extraction from the synchrotron 130, the beam control tray assembly 400 is preferably inserted into the positively charged particle beam proximate the dynamic gantry nozzle 610 as control of the beam shape is preferably done with little space for the beam shape to defocus before striking the tumor. Optionally, insertion and/or retraction of the beam control tray assembly 400 is semi-automated, such as in a manner of a digital-video disk player receiving a digital-video disk, with a selected auto load and/or a selected auto unload feature.

Patient Specific Tray Insert

Referring again to FIG. 5, a system of assembling trays 500 is described. The beam control tray assembly 400 optionally and preferably has interchangeable patient specific tray inserts 510, such as a range shifter insert 511, a patient specific ridge filter insert 512, an aperture insert 513, a compensator insert 514, or a blank insert 515. As described, supra, any of the range shifter insert 511, the patient specific ridge filter insert 512, the aperture insert 513, the compensator insert 514, or the blank insert 515 after insertion into the tray frame 410 are inserted as the beam control tray assembly 400 into the positively charged particle beam path 268, such as proximate the dynamic gantry nozzle 610.

Still referring to FIG. 5, the patient specific tray inserts 510 are further described. The patient specific tray inserts comprise a combination of any of: (1) a standardized beam control insert and (2) a patient specific beam control insert. For example, the range shifter insert or 511 or compensator insert 514 used to control the depth of penetration of the charged particle beam into the patient is optionally: (a) a standard thickness of a beam slowing material, such as a first thickness of Lucite, an acrylic, a clear plastic, and/or a thermoplastic material, (b) one member of a set of members of varying thicknesses and/or densities where each member of the set of members slows the charged particles in the beam path by a known amount, or (c) is a material with a density and thickness designed to slow the charged particles by a customized amount for the individual patient being treated, based on the depth of the individual's tumor in the tissue, the thickness of intervening tissue, and/or the density of intervening bone/tissue. Similarly, the ridge filter insert 512 used to change the focal point or shape of the beam as a function of depth is optionally: (1) selected from a set of ridge filters where different members of the set of ridge filters yield different focal depths or (2) customized for treatment of the individual's tumor based on position of the tumor in the tissue of the individual. Similarly, the aperture insert is: (1) optionally selected from a set of aperture shapes or (2) is a customized individual aperture insert 513 designed for the specific shape of the individual's tumor. The blank insert 515 is an open slot, but serves the purpose of identifying slot occupancy, as described infra.

Slot Occupancy/Identification

Referring again to FIG. 4A, FIG. 4B, and FIG. 5, occupancy and identification of the particular patient specific tray insert 510 into the beam control tray assembly 400 is described. Generally, the beam control tray assembly 400 optionally contains means for identifying, to the main controller 110 and/or a treatment delivery control system described infra, the specific patient tray insert 510 and its location in the charged particle beam path 268. First, the particular tray insert is optionally labeled and/or communicated to the beam control tray assembly 400 or directly to the main controller 110. Second, the beam control tray assembly 400 optionally communicates the tray type and/or tray insert to the main controller 110. In various embodiments, communication of the particular tray insert to the main controller 110 is performed: (1) directly from the tray insert, (2) from the tray insert 510 to the tray assembly 400 and subsequently to the main controller 110, and/or (3) directly from the tray assembly 400. Generally, communication is performed wirelessly and/or via an established electromechanical link. Identification is optionally performed using a radio-frequency identification label, use of a barcode, or the like, and/or via operator input. Examples are provided to further clarify identification of the patient specific tray insert 510 in a given beam control tray assembly 400 to the main controller.

In a first example, one or more of the patient specific tray inserts 510, such as the range shifter insert 511, the patient specific ridge filter insert 512, the aperture insert 513, the compensator insert 514, or the blank insert 515 include an identifier 520 and/or and a first electromechanical identifier plug 530. The identifier 520 is optionally a label, a radio-frequency identification tag, a barcode, a 2-dimensional bar-code, a matrix-code, or the like. The first electromechanical identifier plug 530 optionally includes memory programmed with the particular patient specific tray insert information and a connector used to communicate the information to the beam control tray assembly 400 and/or to the main controller 110. As illustrated in FIG. 5, the first electromechanical identifier plug 530 affixed to the patient specific tray insert 510 plugs into a second electromechanical identifier plug, such as the tray connector/communicator 430, of the beam control tray assembly 400, which is described infra.

In a second example, the beam control tray assembly 400 uses the second electromechanical identifier plug to send occupancy, position, and/or identification information related to the type of tray insert or the patient specific tray insert 510 associated with the beam control tray assembly to the main controller 110. For example, a first tray assembly is configured with a first tray insert and a second tray assembly is configured with a second tray insert. The first tray assembly sends information to the main controller 110 that the first tray assembly holds the first tray insert, such as a range shifter, and the second tray assembly sends information to the main controller 110 that the second tray assembly holds the second tray insert, such as an aperture. The second electromechanical identifier plug optionally contains programmable memory for the operator to input the specific tray insert type, a selection switch for the operator to select the tray insert type, and/or an electromechanical connection to the main controller. The second electromechanical identifier plug associated with the beam control tray assembly 400 is optionally used without use of the first electromechanical identifier plug 530 associated with the tray insert 510.

In a third example, one type of tray connector/communicator 430 is used for each type of patient specific tray insert 510. For example, a first connector/communicator type is used for holding a range shifter insert 511, while a second, third, fourth, and fifth connector/communicator type is used for trays respectively holding a patient specific ridge filter insert 512, an aperture insert 513, a compensator insert 514, or a blank insert 515. In one case, the tray communicates tray type with the main controller. In a second case, the tray communicates patient specific tray insert information with the main controller, such as an aperture identifier custom built for the individual patient being treated.

Tray Insertion/Coupling

Figure 6B:
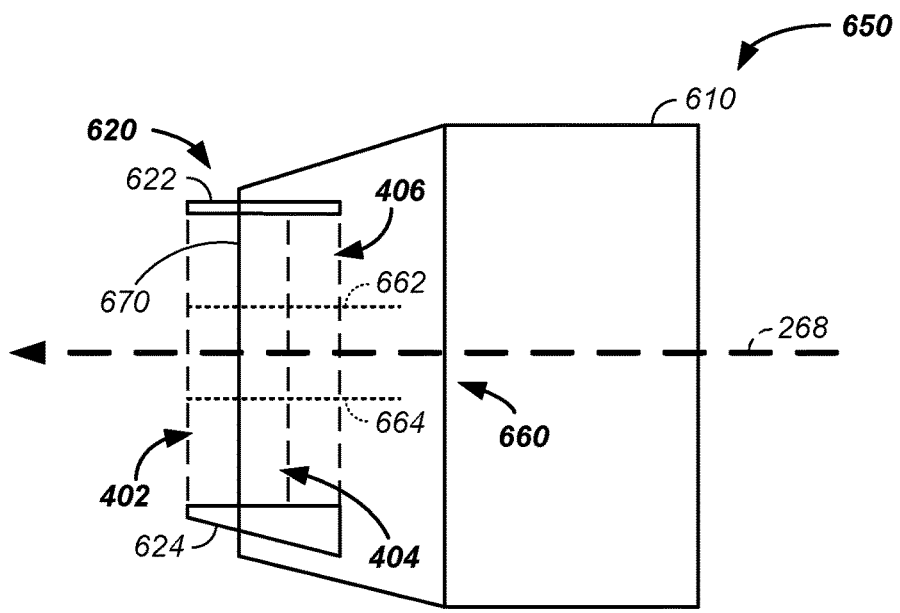

Referring now to FIG. 6A and FIG. 6B a beam control insertion process 600 is described. The beam control insertion process 600 comprises: (1) insertion of the beam control tray assembly 400 and the associated patient specific tray insert 510 into the charged particle beam path 268 and/or dynamic gantry nozzle 610, such as into a tray assembly receiver 620 and (2) an optional partial or total retraction of beam of the tray assembly receiver 620 into the dynamic gantry nozzle 610.

Referring now to FIG. 6A, insertion of one or more of the beam control tray assemblies 400 and the associated patient specific tray inserts 510 into the dynamic gantry nozzle 610 is further described. In FIG. 6A, three beam control tray assemblies, of a possible n tray assemblies, are illustrated, a first tray assembly 402, a second tray assembly 404, and a third tray assembly 406, where n is a positive integer of 1, 2, 3, 4, 5 or more. As illustrated, the first tray assembly 402 slides into a first receiving slot 403, the second tray assembly 404 slides into a second receiving slot 405, and the third tray assembly 406 slides into a third receiving slot 407.

Generally, any tray optionally inserts into any slot or tray types are limited to particular slots through use of a mechanical, physical, positional, and/or steric constraints, such as a first tray type configured for a first insert type having a first size and a second tray type configured for a second insert type having a second distinct size at least ten percent different from the first size.

Still referring to FIG. 6A, identification of individual tray inserts inserted into individual receiving slots is further described. As illustrated, sliding the first tray assembly 402 into the first receiving slot 403 connects the associated electromechanical connector/communicator 430 of the first tray assembly 402 to a first receptor 626. The electromechanical connector/communicator 430 of the first tray assembly communicates tray insert information of the first beam control tray assembly to the main controller 110 via the first receptor 626. Similarly, sliding the second tray assembly 404 into the second receiving slot 405 connects the associated electromechanical connector/communicator 430 of the second tray assembly 404 into a second receptor 627, which links communication of the associated electromechanical connector/communicator 430 with the main controller 110 via the second receptor 627, while a third receptor 628 connects to the electromechanical connected placed into the third slot 407. The non-wireless/direct connection is preferred due to the high radiation levels within the treatment room and the high shielding of the treatment room, which both hinder wireless communication. The connection of the communicator and the receptor is optionally of any configuration and/or orientation.

Tray Receiver Assembly Retraction

Referring again to FIG. 6A and FIG. 6B, retraction of the tray receiver assembly 620 relative to a nozzle end 612 of the dynamic gantry nozzle 610 is described. The tray receiver assembly 620 comprises a framework to hold one or more of the beam control tray assemblies 400 in one or more slots, such as through use of a first tray receiver assembly side 622 through which the beam control tray assemblies 400 are inserted and/or through use of a second tray receiver assembly side 624 used as a backstop, as illustrated holding the plugin receptors configured to receive associated tray connector/communicators 430, such as the first, second, and third receptors 626, 627, 628. Optionally, the tray receiver assembly 620 retracts partially or completely into the dynamic gantry nozzle 610 using a retraction mechanism 660 configured to alternatingly retract and extend the tray receiver assembly 620 relative to a nozzle end 612 of the gantry nozzle 610, such as along a first retraction track 662 and a second retraction track 664 using one or more motors and computer control. Optionally the tray receiver assembly 620 is partially or fully retracted when moving the gantry, nozzle, and/or gantry nozzle 610 to avoid physical constraints of movement, such as potential collision with another object in the patient treatment room.

For clarity of presentation and without loss of generality, several examples of loading patient specific tray inserts into tray assemblies with subsequent insertion into an positively charged particle beam path proximate a gantry nozzle 610 are provided.

In a first example, a single beam control tray assembly 400 is used to control the charged particle beam 268 in the charged particle cancer therapy system 100. In this example, a patient specific range shifter insert 511, which is custom fabricated for a patient, is loaded into a patient specific tray insert 510 to form a first tray assembly 402, where the first tray assembly 402 is loaded into the third receptor 628, which is fully retracted into the gantry nozzle 610.

In a second example, two beam control assemblies 400 are used to control the charged particle beam 268 in the charged particle cancer therapy system 100. In this example, a patient specific ridge filter 512 is loaded into a first tray assembly 402, which is loaded into the second receptor 627 and a patient specific aperture 513 is loaded into a second tray assembly 404, which is loaded into the first receptor 626 and the two associated tray connector/communicators 430 using the first receptor 626 and second receptor 627 communicate to the main controller 110 the patient specific tray inserts 510. The tray receiver assembly 620 is subsequently retracted one slot so that the patient specific ridge filter 512 and the patient specific aperture reside outside of and at the nozzle end 612 of the gantry nozzle 610.

In a third example, three beam control tray assemblies 400 are used, such as a range shifter 511 in a first tray inserted into the first receiving slot 403, a compensator in a second tray inserted into the second receiving slot 405, and an aperture in a third tray inserted into the third receiving slot 407.

Generally, any patient specific tray insert 510 is inserted into a tray frame 410 to form a beam control tray assembly 400 inserted into any slot of the tray receiver assembly 620 and the tray assembly is not retracted or retracted any distance into the gantry nozzle 610.

Tomography/Beam State

In one embodiment, the charged particle tomography apparatus is used to image a tumor in a patient. As current beam position determination/verification is used in both tomography and cancer therapy treatment, for clarity of presentation and without limitation beam state determination is also addressed in this section. However, beam state determination is optionally used separately and without tomography.

In another example, the charged particle tomography apparatus is used in combination with a charged particle cancer therapy system using common elements. For example, tomographic imaging of a cancerous tumor is performed using charged particles generated with an injector, accelerator, and guided with a delivery system that are part of the cancer therapy system, described supra.

In various examples, the tomography imaging system is optionally simultaneously operational with a charged particle cancer therapy system using common elements, allows tomographic imaging with rotation of the patient, is operational on a patient in an upright, semi-upright, and/or horizontal position, is simultaneously operational with X-ray imaging, and/or allows use of adaptive charged particle cancer therapy. Further, the common tomography and cancer therapy apparatus elements are optionally operational in a multi-axis and/or multi-field raster beam mode.

In conventional medical X-ray tomography, a sectional image through a body is made by moving one or both of an X-ray source and the X-ray film in opposite directions during the exposure. By modifying the direction and extent of the movement, operators can select different focal planes, which contain the structures of interest. More modern variations of tomography involve gathering projection data from multiple directions by moving the X-ray source and feeding the data into a tomographic reconstruction software algorithm processed by a computer. Herein, in stark contrast to known methods, the radiation source is a charged particle, such as a proton ion beam or a carbon ion beam. A proton beam is used herein to describe the tomography system, but the description applies to a heavier ion beam, such as a carbon ion beam. Further, in stark contrast to known techniques, herein the radiation source is preferably stationary while the patient is rotated.

Figure 7:
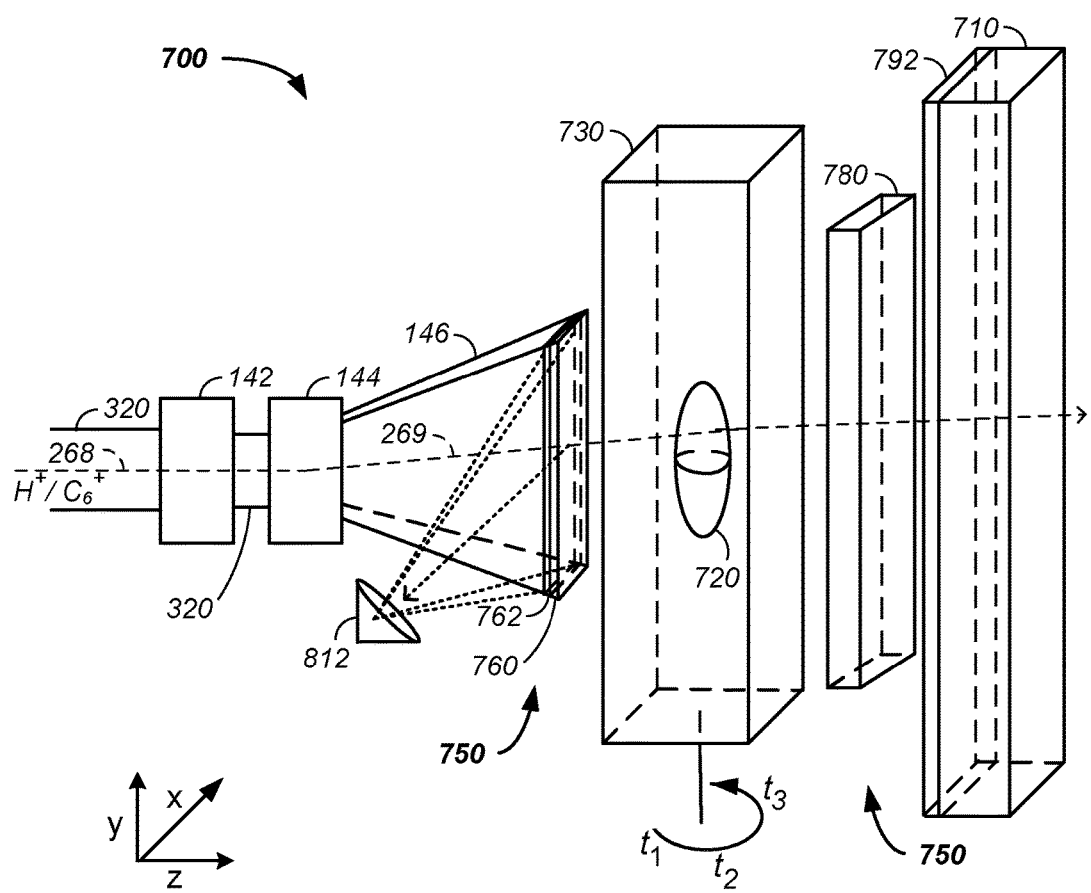
FIG. 7 illustrates a tomography system.

Referring now to FIG. 7, an example of a tomography apparatus is described and an example of a beam state determination is described. In this example, the tomography system 700 uses elements in common with the charged particle beam system 100, including elements of one or more of the injection system 120, accelerator 130, targeting/delivery system 140, patient interface module 150, display system 160, and/or imaging system 170, such as the X-ray imaging system. One or more scintillation plates, such as a scintillating plastic, are used to measure energy, intensity, and/or position of the charged particle beam. For instance, a scintillation plate 710 is positioned behind the patient 730 relative to the targeting/delivery system 140 elements, which is optionally used to measure intensity and/or position of the charged particle beam after transmitting through the patient. Optionally, a second scintillation plate or a charged particle induced photon emitting sheet, described infra, is positioned prior to the patient 730 relative to the targeting/delivery system 140 elements, which is optionally used to measure incident intensity and/or position of the charged particle beam prior to transmitting through the patient. The charged particle beam system 100 as described has proven operation at up to and including 330 MeV, which is sufficient to send protons through the body and into contact with the scintillation material. Particularly, 250 MeV to 330 MeV are used to pass the beam through a standard sized patient with a standard sized pathlength, such as through the chest. The intensity or count of protons hitting the plate as a function of position is used to create an image. The velocity or energy of the proton hitting the scintillation plate is also used in creation of an image of the tumor 720 and/or an image of the patient 730. The patient 730 is rotated about the y-axis and a new image is collected. Preferably, a new image is collected with about every one degree of rotation of the patient resulting in about 360 images that are combined into a tomogram using tomographic reconstruction software. The tomographic reconstruction software uses overlapping rotationally varied images in the reconstruction. Optionally, a new image is collected at about every 2, 3, 4, 5, 10, 15, 30, or 45 degrees of rotation of the patient.

In one embodiment, a tomogram or an individual tomogram section image is collected at about the same time as cancer therapy occurs using the charged particle beam system 100. For example, a tomogram is collected and cancer therapy is subsequently performed: without the patient moving from the positioning systems, such as in a semi-vertical partial immobilization system, a sitting partial immobilization system, or the a laying position. In a second example, an individual tomogram slice is collected using a first cycle of the accelerator 130 and using a following cycle of the accelerator 130, the tumor 720 is irradiated, such as within about 1, 2, 5, 10, 15 or 30 seconds. In a third case, about 2, 3, 4, or 5 tomogram slices are collected using 1, 2, 3, 4, or more rotation positions of the patient 730 within about 5, 10, 15, 30, or 60 seconds of subsequent tumor irradiation therapy.

In another embodiment, the independent control of the tomographic imaging process and X-ray collection process allows simultaneous single and/or multi-field collection of X-ray images and tomographic images easing interpretation of multiple images. Indeed, the X-ray and tomographic images are optionally overlaid to from a hybrid X-ray/proton beam tomographic image as the patient 730 is optionally in the same position for each image.

In still another embodiment, the tomogram is collected with the patient 730 in the about the same position as when the patient's tumor is treated using subsequent irradiation therapy. For some tumors, the patient being positioned in the same upright or semi-upright position allows the tumor 720 to be separated from surrounding organs or tissue of the patient 730 better than in a laying position. Positioning of the scintillation plate 710 behind the patient 730 allows the tomographic imaging to occur while the patient is in the same upright or semi-upright position.

The use of common elements in the tomographic imaging and in the charged particle cancer therapy allows benefits of the cancer therapy, described supra, to optionally be used with the tomographic imaging, such as proton beam x-axis control, proton beam y-axis control, control of proton beam energy, control of proton beam intensity, timing control of beam delivery to the patient, rotation control of the patient, and control of patient translation all in a raster beam mode of proton energy delivery. The use of a single proton or cation beamline for both imaging and treatment facilitates eases patient setup, reduces alignment uncertainties, reduces beam state uncertainties, and eases quality assurance.

In yet still another embodiment, initially a three-dimensional tomographic proton based reference image is collected, such as with hundreds of individual rotation images of the tumor 720 and patient 730. Subsequently, just prior to proton treatment of the cancer, just a few 2-dimensional control tomographic images of the patient are collected, such as with a stationary patient or at just a few rotation positions, such as an image straight on to the patient, with the patient rotated about 45 degrees each way, and/or the patient rotated about 90 degrees each way about the y-axis. The individual control images are compared with the 3-dimensional reference image. An adaptive proton therapy is subsequently performed where: (1) the proton cancer therapy is not used for a given position based on the differences between the 3-dimensional reference image and one or more of the 2-dimensional control images and/or (2) the proton cancer therapy is modified in real time based on the differences between the 3-dimensional reference image and one or more of the 2-dimensional control images.

Charged Particle State Determination/Verification/Photonic Monitoring

Still referring to FIG. 7, the tomography system 700 is optionally used with a charged particle beam state determination system 750, optionally used as a charged particle verification system. The charged particle state determination system 750 optionally measures, determines, and/or verifies one of more of: (1) position of the charged particle beam, (2) direction of the charged particle beam, (3) intensity of the charged particle beam, (4) energy of the charged particle beam, and (5) a history of the charged particle beam.

Figure 8:
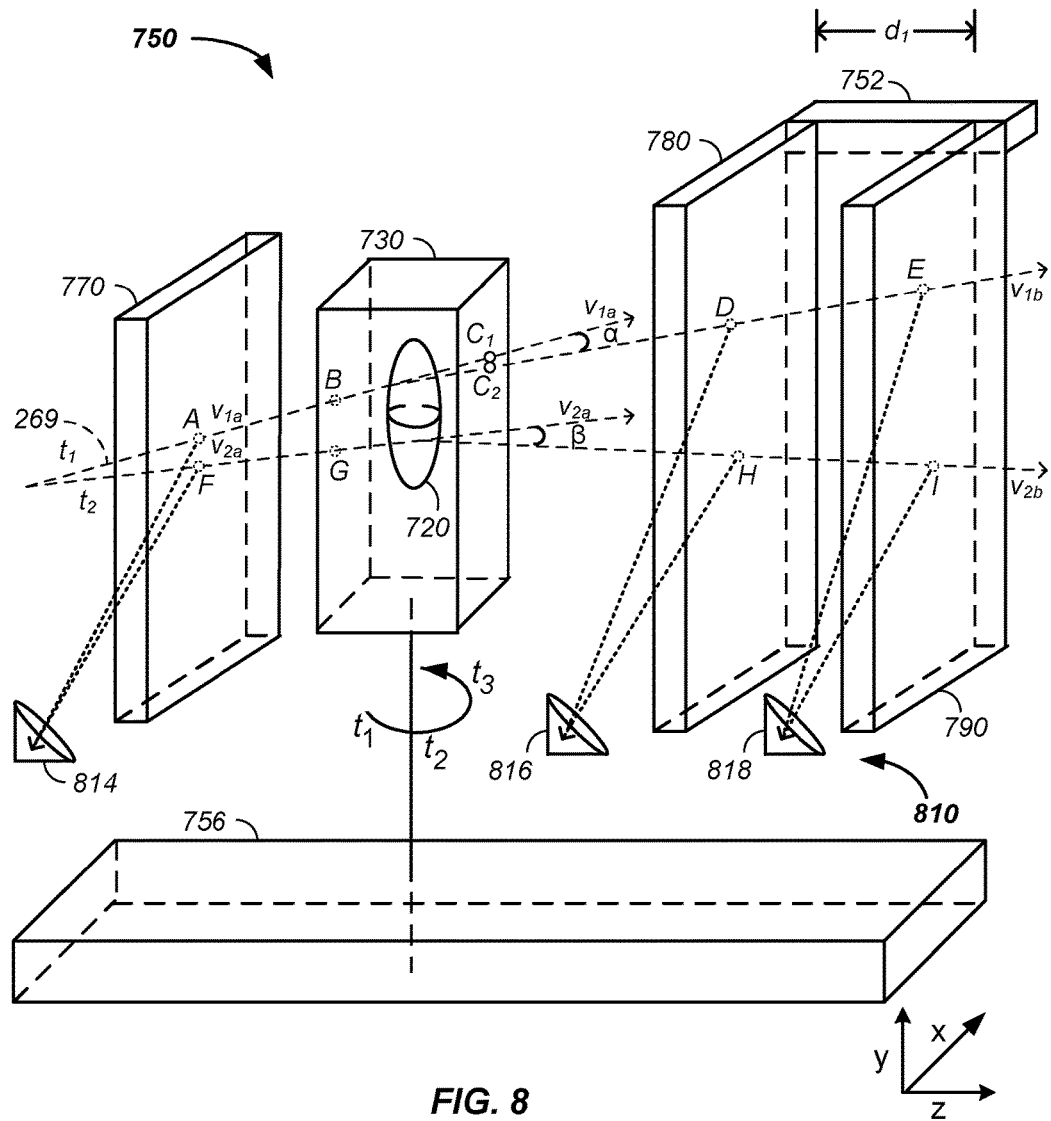
FIG. 8 illustrates a beam path identification system.
Figure 9A:
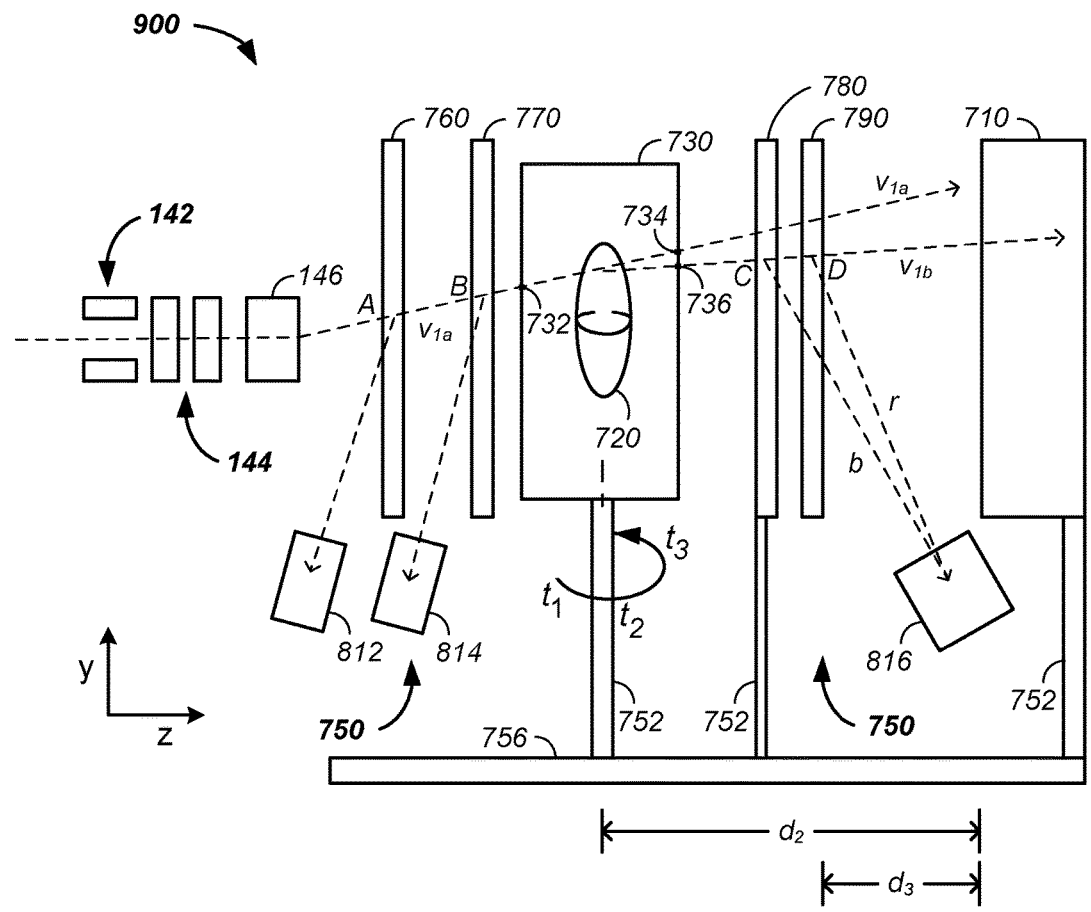
FIG. 9A illustrates a beam path identification system coupled to a beam transport system and a tomography scintillation detector and FIG. 9B illustrates the scintillation detector rotating with the patient and gantry nozzle.

For clarity of presentation and without loss of generality, a description of the charged particle beam state determination system 750 is described and illustrated separately in FIG. 8 and FIG. 9A; however, as described herein elements of the charged particle beam state determination system 750 are optionally and preferably integrated into the nozzle system 146 and/or the tomography system 700 of the charged particle treatment system 100. More particularly, any element of the charged particle beam state determination system 750 is integrated into the nozzle system 146, the dynamic gantry nozzle 610, and/or tomography system 700, such as a surface of the scintillation plate 710 or a surface of a scintillation detector, plate, or system. The nozzle system 146 or the dynamic gantry nozzle 610 provides an outlet of the charged particle beam from the vacuum tube initiating at the injection system 120 and passing through the synchrotron 130 and beam transport system 135. Any plate, sheet, fluorophore, or detector of the charged particle beam state determination system is optionally integrated into the nozzle system 146. For example, an exit foil of the nozzle 610 is optionally a first sheet 760 of the charged particle beam state determination system 750 and a first coating 762 is optionally coated onto the exit foil, as illustrated in FIG. 7. Similarly, optionally a surface of the scintillation plate 710 is a support surface for a fourth coating 792, as illustrated in FIG. 7. The charged particle beam state determination system 750 is further described, infra.

Referring now to FIG. 7, FIG. 8, and FIG. 9A, four sheets, a first sheet 760, a second sheet 770, a third sheet 780, and a fourth sheet 790 are used to illustrated detection sheets and/or photon emitting sheets upon transmittance of a charged particle beam. Each sheet is optionally coated with a photon emitter, such as a fluorophore, such as the first sheet 760 is optionally coated with a first coating 762. Without loss of generality and for clarity of presentation, the four sheets are each illustrated as units, where the light emitting layer is not illustrated. Thus, for example, the second sheet 770 optionally refers to a support sheet, a light emitting sheet, and/or a support sheet coated by a light emitting element. The four sheets are representative of n sheets, where n is a positive integer.

Referring now to FIG. 7 and FIG. 8, the charged particle beam state verification system 750 is a system that allows for monitoring of the actual charged particle beam position in real-time without destruction of the charged particle beam. The charged particle beam state verification system 750 preferably includes a first position element or first beam verification layer, which is also referred to herein as a coating, luminescent, fluorescent, phosphorescent, radiance, or viewing layer. The first position element optionally and preferably includes a coating or thin layer substantially in contact with a sheet, such as an inside surface of the nozzle foil, where the inside surface is on the synchrotron side of the nozzle foil. Less preferably, the verification layer or coating layer is substantially in contact with an outer surface of the nozzle foil, where the outer surface is on the patient treatment side of the nozzle foil. Preferably, the nozzle foil provides a substrate surface for coating by the coating layer. Optionally, a binding layer is located between the coating layer and the nozzle foil, substrate, or support sheet. Optionally, the position element is placed anywhere in the charged particle beam path. Optionally, more than one position element on more than one sheet, respectively, is used in the charged particle beam path and is used to determine a state property of the charged particle beam, as described infra.

Still referring to FIG. 7 and FIG. 8, the coating, referred to as a fluorophore, yields a measurable spectroscopic response, spatially viewable by a detector or camera, as a result of transmission by the proton beam. The coating is preferably a phosphor, but is optionally any material that is viewable or imaged by a detector where the material changes spectroscopically as a result of the charged particle beam hitting or transmitting through the coating or coating layer. A detector or camera views secondary photons emitted from the coating layer and determines a position of a treatment beam 269, which is also referred to as a current position of the charged particle beam or final treatment vector of the charged particle beam, by the spectroscopic differences resulting from protons and/or charged particle beam passing through the coating layer. For example, the camera views a surface of the coating surface as the proton beam or positively charged cation beam is being scanned by the first axis control 142, vertical control, and the second axis control 144, horizontal control, beam position control elements during treatment of the tumor 720. The camera views the current position of the charged particle beam or treatment beam 269 as measured by spectroscopic response. The coating layer is preferably a phosphor or luminescent material that glows and/or emits photons for a short period of time, such as less than 5 seconds for a 50% intensity, as a result of excitation by the charged particle beam. The detector observes the temperature change and/or observe photons emitted from the charged particle beam traversed spot. Optionally, a plurality of cameras or detectors are used, where each detector views all or a portion of the coating layer. For example, two detectors are used where a first detector views a first half of the coating layer and the second detector views a second half of the coating layer. Preferably, at least a portion of the detector is mounted into the nozzle system to view the proton beam position after passing through the first axis and second axis controllers 142, 144. Preferably, the coating layer is positioned in the proton beam path 268 in a position prior to the protons striking the patient 730.

Figure 10:
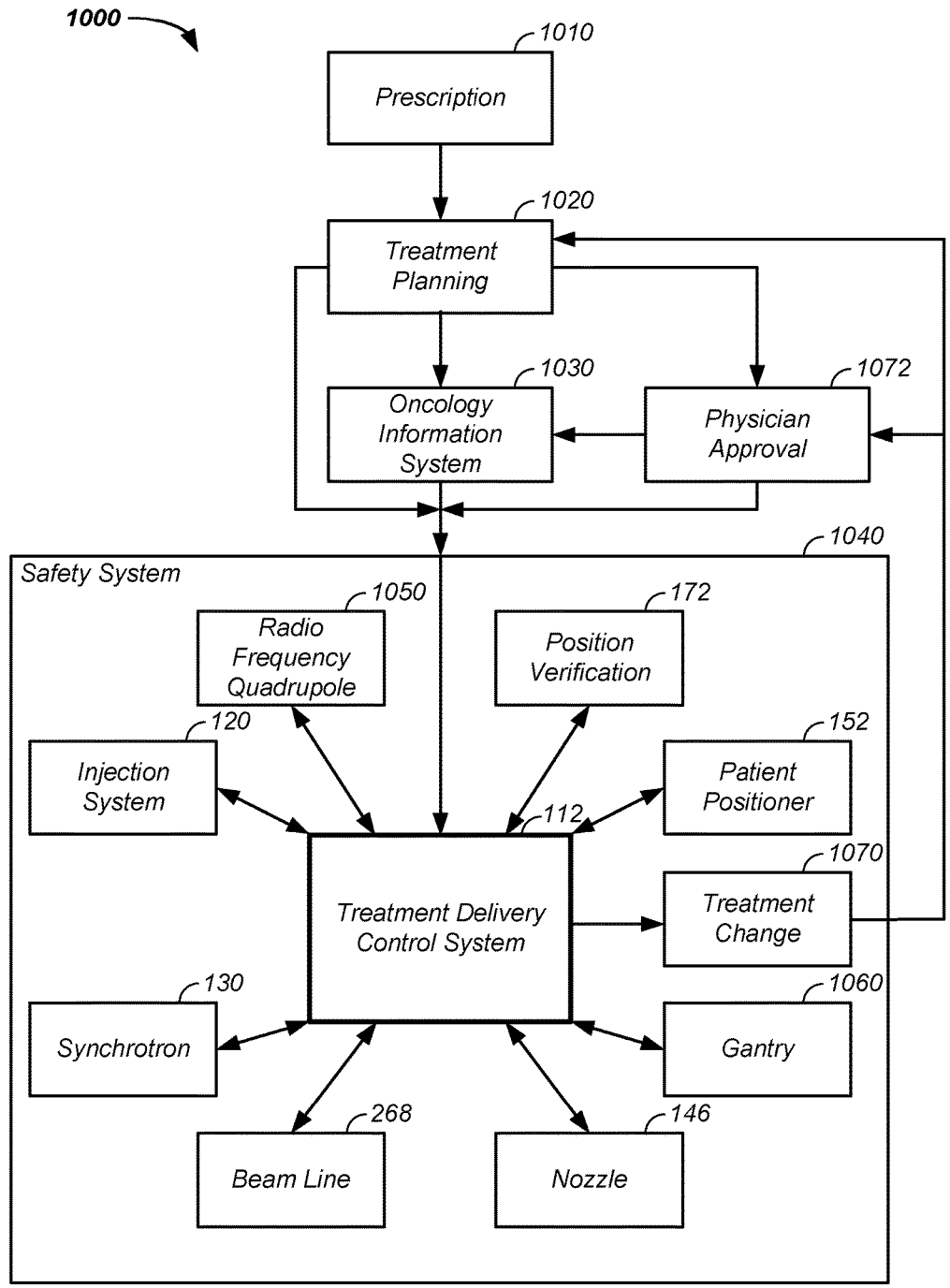
FIG. 10 illustrates a treatment delivery control system.

Referring now to FIG. 1 and FIG. 7, the main controller 110, connected to the camera or detector output, optionally and preferably compares the final proton beam position or position of the treatment beam 269 with the planned proton beam position and/or a calibration reference to determine if the actual proton beam position or position of the treatment beam 269 is within tolerance. The charged particle beam state determination system 750 preferably is used in one or more phases, such as a calibration phase, a mapping phase, a beam position verification phase, a treatment phase, and a treatment plan modification phase. The calibration phase is used to correlate, as a function of x-, y-position of the glowing response the actual x-, y-position of the proton beam at the patient interface. During the treatment phase, the charged particle beam position is monitored and compared to the calibration and/or treatment plan to verify accurate proton delivery to the tumor 720 and/or as a charged particle beam shutoff safety indicator. Referring now to FIG. 10, the position verification system 172 and/or the treatment delivery control system 112, upon determination of a tumor shift, an unpredicted tumor distortion upon treatment, and/or a treatment anomaly optionally generates and or provides a recommended treatment change 1070. The treatment change 1070 is optionally sent out while the patient 730 is still in the treatment position, such as to a proximate physician or over the internet to a remote physician, for physician approval 1072, receipt of which allows continuation of the now modified and approved treatment plan.

EXAMPLE I

Referring now to FIG. 7, a first example of the charged particle beam state determination system 750 is illustrated using two cation induced signal generation surfaces, referred to herein as the first sheet 760 and a third sheet 780. Each sheet is described below.

Still referring to FIG. 7, in the first example, the optional first sheet 760, located in the charged particle beam path prior to the patient 730, is coated with a first fluorophore coating 762, wherein a cation, such as in the charged particle beam, transmitting through the first sheet 760 excites localized fluorophores of the first fluorophore coating 762 with resultant emission of one or more photons. In this example, a first detector 812 images the first fluorophore coating 762 and the main controller 110 determines a current position of the charged particle beam using the image of the fluorophore coating 762 and the detected photon(s). The intensity of the detected photons emitted from the first fluorophore coating 762 is optionally used to determine the intensity of the charged particle beam used in treatment of the tumor 720 or detected by the tomography system 700 in generation of a tomogram and/or tomographic image of the tumor 720 of the patient 730. Thus, a first position and/or a first intensity of the charged particle beam is determined using the position and/or intensity of the emitted photons, respectively.

Still referring to FIG. 7, in the first example, the optional third sheet 780, positioned posterior to the patient 730, is optionally a cation induced photon emitting sheet as described in the previous paragraph. However, as illustrated, the third sheet 780 is a solid state beam detection surface, such as a detector array. For instance, the detector array is optionally a charge coupled device, a charge induced device, CMOS, or camera detector where elements of the detector array are read directly, as does a commercial camera, without the secondary emission of photons. Similar to the detection described for the first sheet, the third sheet 780 is used to determine a position of the charged particle beam and/or an intensity of the charged particle beam using signal position and/or signal intensity from the detector array, respectively.

Still referring to FIG. 7, in the first example, signals from the first sheet 760 and third sheet 780 yield a position before and after the patient 730 allowing a more accurate determination of the charged particle beam through the patient 730 therebetween. Optionally, knowledge of the charged particle beam path in the targeting/delivery system 740, such as determined via a first magnetic field strength across the first axis control 142 or a second magnetic field strength across the second axis control 144 is combined with signal derived from the first sheet 760 to yield a first vector of the charged particles prior to entering the patient 730 and/or an input point of the charged particle beam into the patient 730, which also aids in: (1) controlling, monitoring, and/or recording tumor treatment and/or (2) tomography development/interpretation. Optionally, signal derived from use of the third sheet 780, posterior to the patient 730, is combined with signal derived from tomography system 700, such as the scintillation plate 710, to yield a second vector of the charged particles posterior to the patient 730 and/or an output point of the charged particle beam from the patient 730, which also aids in: (1) controlling, monitoring, deciphering, and/or (2) interpreting a tomogram or a tomographic image.

For clarity of presentation and without loss of generality, detection of photons emitted from sheets is used to further describe the charged particle beam state determination system 750. However, any of the cation induced photon emission sheets described herein are alternatively detector arrays. Further, any number of cation induced photon emission sheets are used prior to the patient 730 and/or posterior to the patient 730, such a 1, 2, 3, 4, 6, 8, 10, or more. Still further, any of the cation induced photon emission sheets are place anywhere in the charged particle beam, such as in the synchrotron 130, in the beam transport system 135, in the targeting/delivery system 140, the nozzle 146, in the gantry room, and/or in the tomography system 700. Any of the cation induced photon emission sheets are used in generation of a beam state signal as a function of time, which is optionally recorded, such as for an accurate history of treatment of the tumor 720 of the patient 730 and/or for aiding generation of a tomographic image.

EXAMPLE II

Referring now to FIG. 8, a second example of the charged particle beam state determination system 750 is illustrated using three cation induced signal generation surfaces, referred to herein as the second sheet 770, the third sheet 780, and the fourth sheet 790. Any of the second sheet 770, the third sheet 780, and the fourth sheet 790 contain any of the features of the sheets described supra.

Still referring to FIG. 8, in the second example, the second sheet 770, positioned prior to the patient 730, is optionally integrated into the nozzle 146, but is illustrated as a separate sheet. Signal derived from the second sheet 770, such as at point A, is optionally combined with signal from the first sheet 760 and/or state of the targeting/delivery system 140 to yield a first vector, $v_{1a}$, from point A to point B of the charged particle beam prior to the sample or patient 730 at a first time, $t_1$, and a second vector, $v_{2a}$, from point F to point G of the charged particle beam prior to the sample at a second time, $t_2$.

Still referring to FIG. 8, in the second example, the third sheet 780 and the fourth sheet 790, positioned posterior to the patient 730, are optionally integrated into the tomography system 700, but are illustrated as a separate sheets. Signal derived from the third sheet 780, such as at point D, is optionally combined with signal from the fourth sheet 790 and/or signal from the tomography system 700 to yield a first vector, $v_{1b}$, from point $C_2$ to point D and/or from point D to point E of the charged particle beam posterior to the patient 730 at the first time, $t_1$, and a second vector, $v_{2a}$, such as from point H to point I of the charged particle beam posterior to the sample at a second time, $t_2$. Signal derived from the third sheet 780 and/or from the fourth sheet 790 and the corresponding first vector at the second time, $t_2$, is used to determine an output point, $C_2$, which may and often does differ from an extension of the first vector, $v_{1a}$, from point A to point B through the patient to a non-scattered beam path of point $C_1$. The difference between point $C_1$ and point $C_2$ and/or an angle, a, between the first vector at the first time, $v_{1a}$, and the first vector at the second time, $v_{1b}$, is used to determine/map/identify, such as via tomographic analysis, internal structure of the patient 730, sample, and/or the tumor 720, especially when combined with scanning the charged particle beam in the x/y-plane as a function of time, such as illustrated by the second vector at the first time, $v_{2a}$, and the second vector at the second time, $v_{2b}$, forming angle β and/or with rotation of the patient 730, such as about the y-axis, as a function of time.

Still referring to FIG. 8, multiple detectors/detector arrays are illustrated for detection of signals from multiple sheets, respectively. However, a single detector/detector array is optionally used to detect signals from multiple sheets, as further described infra. As illustrated, a set of detectors 810 is illustrated, including a second detector 814 imaging the second sheet 770, a third detector 816 imaging the third sheet 780, and a fourth detector 818 imaging the fourth sheet 790. Any of the detectors described herein are optionally detector arrays, are optionally coupled with any optical filter, and/or optionally use one or more intervening optics to image any of the four sheets 760, 770, 780, 790. Further, two or more detectors optionally image a single sheet, such as a region of the sheet, to aid optical coupling, such as F-number optical coupling.

Still referring to FIG. 8, a vector of the charged particle beam is determined. Particularly, in the illustrated example, the third detector 816, determines, via detection of secondary emitted photons, that the charged particle beam transmitted through point D and the fourth detector 818 determines that the charged particle beam transmitted through point E, where points D and E are used to determine the first vector at the second time, $v_{1b}$, as described supra. To increase accuracy and precision of a determined vector of the charged particle beam, a first determined beam position and a second determined beam position are optionally and preferably separated by a distance, $d_1$, such as greater than 0.1, 0.5, 1, 2, 3, 5, 10, or more centimeters. A support element 752 is illustrated that optionally connects any two or more elements of the charged particle beam state determination system 750 to each other and/or to any element of the charged particle beam system 100, such as a rotating platform 756 used to co-rotate the patient 730 and any element of the tomography system 700.

EXAMPLE III

Still referring to FIG. 9A, a third example of the charged particle beam state determination system 750 is illustrated in an integrated tomography-cancer therapy system 900.

Referring to FIG. 9A, multiple sheets and multiple detectors are illustrated determining a charged particle beam state prior to the patient 730. As illustrated, a first camera 812 spatially images photons emitted from the first sheet 760 at point A, resultant from energy transfer from the passing charged particle beam, to yield a first signal and a second camera 814 spatially images photons emitted from the second sheet 770 at point B, resultant from energy transfer from the passing charged particle beam, to yield a second signal. The first and second signals allow calculation of the first vector, $v_{1a}$, with a subsequent determination of an entry point 732 of the charged particle beam into the patient 730. Determination of the first vector, $v_{1a}$, is optionally supplemented with information derived from states of the magnetic fields about the first axis control 142, the vertical control, and the second axis control 144, the horizontal axis control, as described supra.

Still referring to FIG. 9A, the charged particle beam state determination system is illustrated with multiple resolvable wavelengths of light emitted as a result of the charged particle beam transmitting through more than one molecule type, light emission center, and/or fluorophore type. For clarity of presentation and without loss of generality a first fluorophore in the third sheet 780 is illustrated as emitting blue light, b, and a second fluorophore in the fourth sheet 790 is illustrated as emitting red light, r, that are both detected by the third detector 816. The third detector is optionally coupled with any wavelength separation device, such as an optical filter, grating, or Fourier transform device. For clarity of presentation, the system is described with the red light passing through a red transmission filter blocking blue light and the blue light passing through a blue transmission filter blocking red light. Wavelength separation, using any means, allows one detector to detect a position of the charged particle beam resultant in a first secondary emission at a first wavelength, such as at point C, and a second secondary emission at a second wavelength, such as at point D. By extension, with appropriate optics, one camera is optionally used to image multiple sheets and/or sheets both prior to and posterior to the sample. Spatial determination of origin of the red light and the blue light allow calculation of the first vector at the second time, $V_{1b}$, and an actual exit point 736 from the patient 730 as compared to a non-scattered exit point 734 from the patient 730 as determined from the first vector at the first time, $V_{1a}$.

Figure 9B:
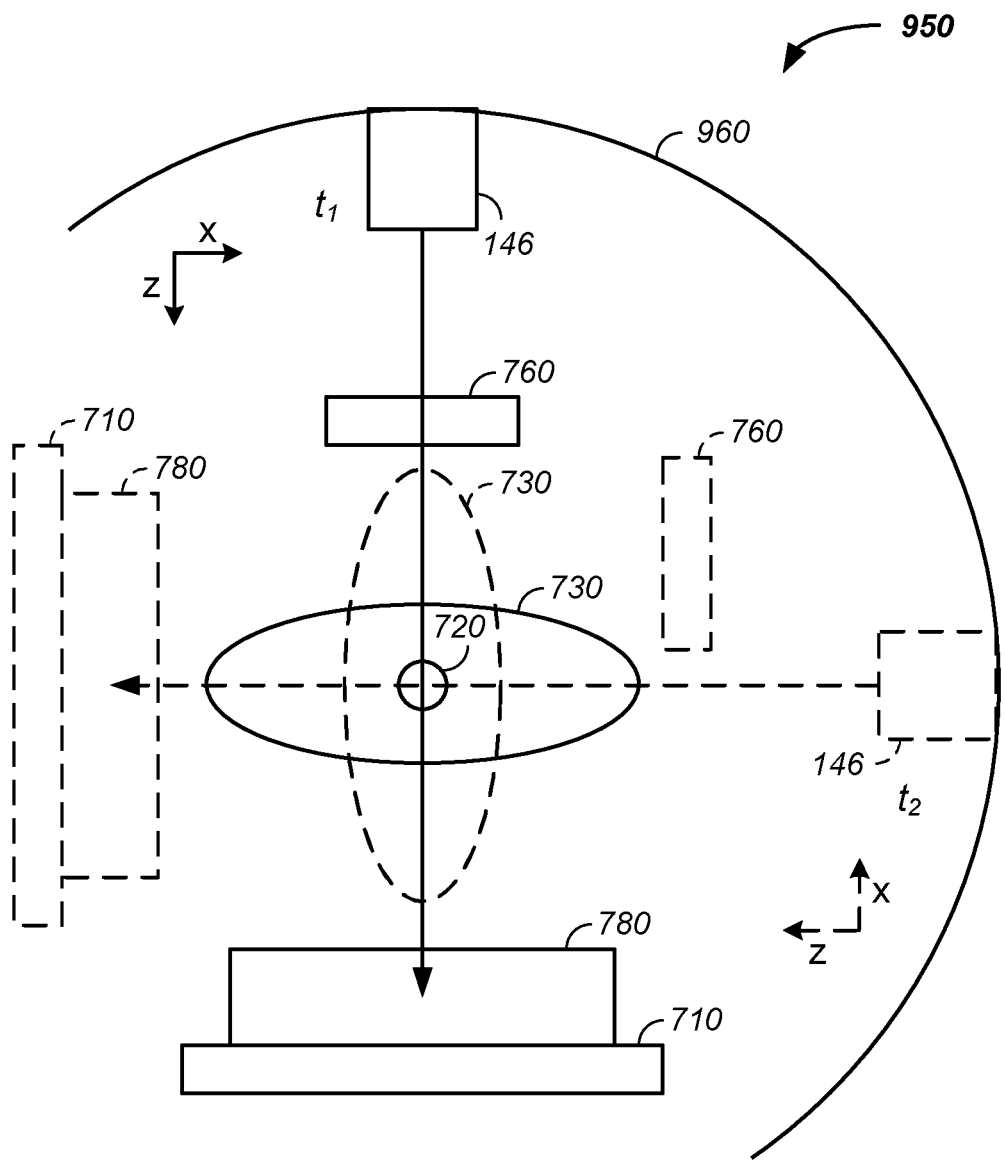

Still referring to FIG. 9A and referring now to FIG. 9B, the integrated tomography-cancer therapy system 900 is illustrated with an optional configuration of elements of the charged particle beam state determination system 750 being co-rotatable with the nozzle 146 of the cancer therapy system 100. More particularly, in one case sheets of the charged particle beam state determination system 750 positioned prior to, posterior to, or on both sides of the patient 730 co-rotate with the scintillation plate 710 about any axis, such as illustrated with rotation about the y-axis. Further, any element of the charged particle beam state determination system 750, such as a detector, two-dimensional detector, multiple two-dimensional detectors, and/or light coupling optic move as the gantry moves, such as along a common arc of movement of the nozzle 146 and/or at a fixed distance to the common arc. For instance, as the gantry moves, a monitoring camera positioned on the opposite side of the tumor 720 or patient 730 from the nozzle 146 maintains a position on the opposite side of the tumor 720 or patient 730. In various cases, co-rotation is achieved by co-rotation of the gantry of the charged particle beam system and a support of the patient, such as the rotatable platform 756, which is also referred to herein as a movable or dynamically positionable patient platform, patient chair, or patient couch. Mechanical elements, such as the support element 752 affix the various elements of the charged particle beam state determination system 750 relative to each other, relative to the nozzle 146, and/or relative to the patient 730. For example, the support elements 752 maintain a second distance, $d_2$, between a position of the tumor 720 and the third sheet 780 and/or maintain a third distance, $d_3$, between a position of the third sheet 780 and the scintillation plate 710. More generally, support elements 752 optionally dynamically position any element about the patient 730 relative to one another or in x,y,z-space in a patient diagnostic/treatment room, such as via computer control.

Referring now to FIG. 9B, positioning the nozzle 146 of a gantry 960 on an opposite side of the patient 730 from a detection surface, such as the scintillation plate 710, in a gantry movement system 950 is described. Generally, in the gantry movement system 950, as the gantry 960 rotates about an axis the nozzle 146 and/or one or more magnets of the beam transport system 135 are repositioned. As illustrated, the nozzle 146 is positioned by the gantry 960 in a first position at a first time, $t_1$, and in a second position at a second time, $t_2$, where n positions are optionally possible. An electromechanical system 712, such as a patient table, patient couch, patient couch, and/or a scintillation plate holder maintains the patient 730 between the nozzle 146 and the scintillation plate 710 of the tomography system 700. Similarly, not illustrated for clarity of presentation, the electromechanical system 712 maintains a position of the third sheet 780 and/or a position of the fourth sheet 790 on a posterior or opposite side of the patient 730 from the nozzle 146 as the gantry 960 rotates or moves the nozzle 146. Similarly, the electromechanical system 712 maintains a position of the first sheet 760 or first screen and/or a position of the second sheet 770 or second screen on a same or prior side of the patient 730 from the nozzle 146 as the gantry 960 rotates or moves the nozzle 146. As illustrated, the electromechanical system 712 optionally positions the first sheet 760 in the positively charged particle path at the first time, $t_1$, and rotates, pivots, and/or slides the first sheet 760 out of the positively charged particle path at the second time, $t_2$. The electromechanical system 712 is optionally and preferably connected to the main controller 110 and/or the treatment delivery control system 112. The electromechanical system 712 optionally maintains a fixed distance between: (1) the patient and the nozzle 146 or the nozzle end 612, (2) the patient 730 or tumor 720 and the scintillation plate 710, and/or (3) the nozzle 146 and the scintillation plate 710 at a first treatment time with the gantry 960 in a first position and at a second treatment time with the gantry 960 in a second position. Use of a common charged particle beam path for both imaging and cancer treatment and/or maintaining known or fixed distances between beam transport/guide elements and treatment and/or detection surface enhances precision and/or accuracy of a resultant image and/or tumor treatment, such as described supra.

System Integration

Any of the systems and/or elements described herein are optionally integrated together and/or are optionally integrated with known systems.

Treatment Delivery Control System

Referring now to FIG. 10, a centralized charged particle treatment system 1000 is illustrated. Generally, once a charged particle therapy plan is devised, a central control system or treatment delivery control system 112 is used to control sub-systems while reducing and/or eliminating direct communication between major subsystems. Generally, the treatment delivery control system 112 is used to directly control multiple subsystems of the cancer therapy system without direct communication between selected subsystems, which enhances safety, simplifies quality assurance and quality control, and facilitates programming. For example, the treatment delivery control system 112 directly controls one or more of: an imaging system, a positioning system, an injection system, a radio-frequency quadrupole system, a linear accelerator, a ring accelerator or synchrotron, an extraction system, a beam line, an irradiation nozzle, a gantry, a display system, a targeting system, and a verification system. Generally, the control system integrates subsystems and/or integrates output of one or more of the above described cancer therapy system elements with inputs of one or more of the above described cancer therapy system elements.

Still referring to FIG. 10, an example of the centralized charged particle treatment system 1000 is provided. Initially, a doctor, such as an oncologist, prescribes 1010 or recommends tumor therapy using charged particles. Subsequently, treatment planning 1020 is initiated and output of the treatment planning step 1020 is sent to an oncology information system 1030 and/or is directly sent to the treatment delivery system 112, which is an example of the main controller 110.

Still referring to FIG. 10, the treatment planning step 1020 is further described. Generally, radiation treatment planning is a process where a team of oncologist, radiation therapists, medical physicists, and/or medical dosimetrists plan appropriate charged particle treatment of a cancer in a patient. Typically, one or more imaging systems 170 are used to image the tumor and/or the patient, described infra. Planning is optionally: (1) forward planning and/or (2) inverse planning. Cancer therapy plans are optionally assessed with the aid of a dose-volume histogram, which allows the clinician to evaluate the uniformity of the dose to the tumor and surrounding healthy structures. Typically, treatment planning is almost entirely computer based using patient computed tomography data sets using multimodality image matching, image coregistration, or fusion.

Forward Planning

In forward planning, a treatment oncologist places beams into a radiotherapy treatment planning system including: how many radiation beams to use and which angles to deliver each of the beams from. This type of planning is used for relatively simple cases where the tumor has a simple shape and is not near any critical organs.

Inverse Planning

In inverse planning, a radiation oncologist defines a patient's critical organs and tumor and gives target doses and importance factors for each. Subsequently, an optimization program is run to find the treatment plan which best matches all of the input criteria.

Oncology Information System

Still referring to FIG. 10, the oncology information system 1030 is further described. Generally, the oncology information system 1030 is one or more of: (1) an oncology-specific electronic medical record, which manages clinical, financial, and administrative processes in medical, radiation, and surgical oncology departments; (2) a comprehensive information and image management system; and (3) a complete patient information management system that centralizes patient data; and (4) a treatment plan provided to the charged particle beam system 100, main controller 110, and/or the treatment delivery control system 112. Generally, the oncology information system 1030 interfaces with commercial charged particle treatment systems.

Safety System/Treatment Delivery Control System

Still referring to FIG. 10, the treatment delivery control system 112 is further described. Generally, the treatment delivery control system 112 receives treatment input, such as a charged particle cancer treatment plan from the treatment planning step 1020 and/or from the oncology information system 1030 and uses the treatment input and/or treatment plan to control one or more subsystems of the charged particle beam system 100. The treatment delivery control system 112 is an example of the main controller 110, where the treatment delivery control system receives subsystem input from a first subsystem of the charged particle beam system 100 and provides to a second subsystem of the charged particle beam system 100: (1) the received subsystem input directly, (2) a processed version of the received subsystem input, and/or (3) a command, such as used to fulfill requisites of the treatment planning step 1020 or direction of the oncology information system 1030. Generally, most or all of the communication between subsystems of the charged particle beam system 100 go to and from the treatment delivery control system 112 and not directly to another subsystem of the charged particle beam system 100. Use of a logically centralized treatment delivery control system has many benefits, including: (1) a single centralized code to maintain, debug, secure, update, and to perform checks on, such as quality assurance and quality control checks; (2) a controlled logical flow of information between subsystems; (3) an ability to replace a subsystem with only one interfacing code revision; (4) room security; (5) software access control; (6) a single centralized control for safety monitoring; and (7) that the centralized code results in an integrated safety system 1040 encompassing a majority or all of the subsystems of the charged particle beam system 100. Examples of subsystems of the charged particle cancer therapy system 100 include: a radio frequency quadrupole 1050, a radio frequency quadrupole linear accelerator, the injection system 120, the synchrotron 130, the accelerator system 132, the extraction system 134, any controllable or monitorable element of the beam line 268, the targeting/delivery system 140, the nozzle 146, a gantry 1060 or an element of the gantry 1060, the patient interface module 150, a patient positioner 152, the display system 160, the imaging system 170, a patient position verification system 172, any element described supra, and/or any subsystem element. A treatment change 1070 at time of treatment is optionally computer generated with or without the aid of a technician or physician and approved while the patient is still in the treatment room, in the treatment chair, and/or in a treatment position.

Safety

Figure 11:
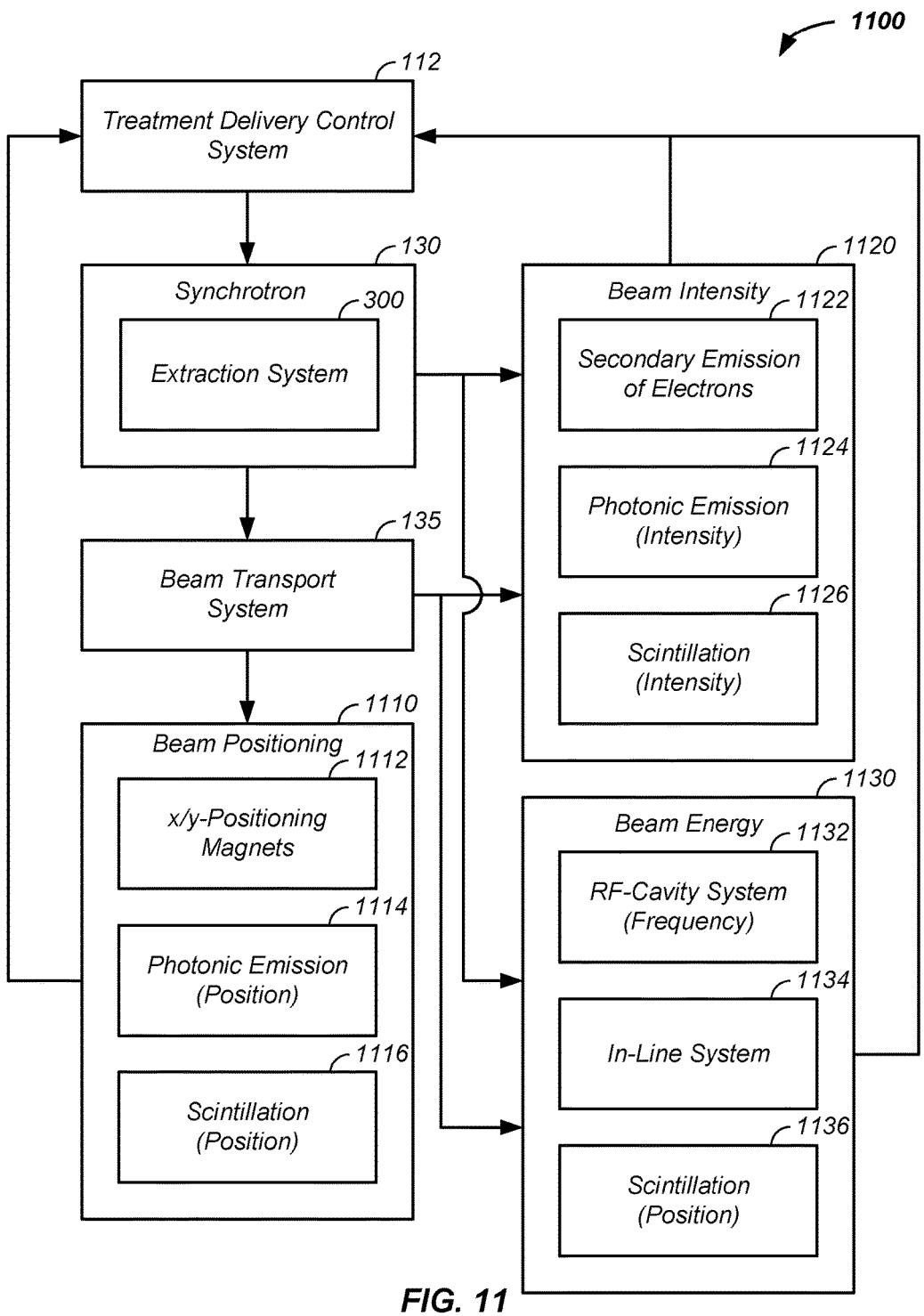
FIG. 11 illustrates beam state determination systems.

Referring now to FIG. 11, a redundant safety system 1100 is described. In one optional and preferred embodiment, the charged particle beam system 100 includes redundant systems for determination of one or more of: (1) beam position, (2) beam direction, (3) beam intensity, (4) beam energy, and (5) beam shape. The redundant safety system 1000 is further described herein.

Beam Position

A beam positioning system 1110 or beam position determination/verification system is linked to the main controller 100 or treatment delivery control system 112. The beam positioning system 1110 includes any electromechanical system, optical system, and/or calculation for determining a current position of the charged particle beam. In a first case, after calibration, the scanning/targeting/delivery system 140 uses x/y-positioning magnets, such as in the first axis control 142 and the second axis control 144, to position the charged particle beam. In a second case, a photonic emission position system 1114 is used to measure a position of the charged particle beam, where the photonic emission system 1114 uses a secondary emission of a photon upon passage of the charged particle beam, such as described supra for the first sheet 760, the second sheet 770, the third sheet 780, and the fourth sheet 790. In a third a case, a scintillation positioning system 1116, such as via use of a detector element in the tomography system 700, is used to measure a position of the charged particle beam. Any permutation or combination of the three cases described herein yield multiple or redundant measures of the charged particle beam position and therefrom one or more measures of a charged particle beam vector during a period of time.

Beam Intensity

A beam intensity system 1120 or beam intensity determination/verification system is linked to the main controller 100 or treatment delivery control system 112. Herein, intensity is a number of positively charged particles passing a point or plane as a function of time. The beam intensity system 1110 includes any electromechanical system, optical system, and/or calculation for determining a current intensity of the charged particle beam. In a first case, the extraction system 134 uses an electron emission system 1122, such as a secondary emission of electrons upon passage of the charged particle beam through the extraction material 330, to determine an intensity of the charged particle beam. In a second case, the duration of the applied RF-field and/or a magnitude of the RF-field applied in the RF-cavity system 310 is used to calculate the intensity of the charged particle beam, as described supra. In a third case, a photon emission system 1124, such as a magnitude of a signal representing the emitted photons from the photonic emission system 1114, is used to measure the intensity of the charged particle beam. In a fourth case, a scintillation intensity determination system 1126 measures the intensity of the charged particle beam, such as with a detector of the tomography system 700.

Beam Energy

A beam energy system 1130 or beam energy determination/verification system is linked to the main controller 100 or treatment delivery control system 112. Herein, energy is optionally referred to as a velocity of the positively charged particles passing a point, where energy is dependent upon mass of the charged particles. The beam energy system 1110 includes any electromechanical system, optical system, and/or calculation for determining a current energy of the charged particle beam. In a first case, an RF-cavity energy system 1132 calculates an energy of the charged particles in the charged particle beam, such as via relating a period of an applied RF-field in the RF-cavity system 310 to energy, such as described supra. In a second case, an in-line energy system 1134 is used to measure a value related to beam energy, such as described above in equations 1 and 2. In a third case, a scintillation energy system 1136 is used to measure an energy of the charged particle beam, such as via use of a detector in the tomography system 700.

Optionally and preferably, two or more measures/determination/calculations of a beam state property, such as position, direction, shape, intensity, and/or energy yield a redundant measure of the measured state for use in a beam safety system and/or an emergency beam shut-off system. Optionally and preferably, the two or more measures of a beam state property are used to enhance precision and/or accuracy of determination of the beam state property through statistical means. Optionally and preferably, any of the beam state properties are recorded and/or used to predict a future state, such as position, intensity, and/or energy of the charged particle beam, such as in a neighboring voxel in the tumor 720 adjacent to a currently treated voxel in the tumor 720 of the patient 730.

Motion Control System

Referring now to FIG. 12A, a motion control system 1200 is illustrated. Generally, the motion control system controls, as a function of time: (1) the charged particle beam state, such as direction, shape, intensity, and/or energy; (2) a patient position; and/or (3) an imaging system. The motion control system 1200 is further described herein.

The motion control system 1200 optionally uses one or more patient interface controllers 1210, such as an external motion control system 1212, an internal motion control system 1214, an external pendant 1216, and an internal pendant 1218. As illustrated, the patient 730 is in a treatment room 1222 separated from a control room 1224 by a radiation shielded wall 1226 and a window 1228 or view port. The external motion control system 1212, internal motion control system 1214, external pendant 1216, and the internal pendant 1218 optionally and preferably control the same elements, allowing one or more operators control of the motion control system. Any of the patient interface controllers 1210 are optionally linked to each other or to the main controller 110 via wireless means; however, interconnections of the patient interface controllers 1210 to each other and/or to the main controller 110 are preferably hard-wired due to high radiation levels in the treatment room 1222. For example, the external pendant 1216 is linked via a first communication bundle 1217 to the external motion control system 1212, the internal pendant 1218 is linked via a second communication bundle 1219 to the internal motion system controller 1214, and/or the internal and external motion control system 1212, 1214 are hardwired to each other and/or to the main controller 110. The first communication bundle 1217 and the second communication bundle 1219 optionally provide power to the external pendant 1216 and the internal pendant 1218, respectively. The second communication bundle 1219 is optionally attached and/or linked to the nozzle system 146 and/or an element of the beam transport system 135 to keep the second communication bundle: (1) accessible to the operator, (2) out of the way of the charged particle beam, and/or (3) out of the way of motion of the patient 730/patient interface module 150. Optionally, a patient specific treatment module 1290 is replaceably plugged into and/or attached to the one or more patient interface controllers 1210, such as the internal pendant 1218. The patient treatment module 1290 optionally contains one or more of: image information about the individual being treated and/or preprogrammed treatment steps for the individual being treated, where some controls of the charged particle beam system 100, such as related to charged particle beam aiming and/or patient positioning are optionally limited by the preprogrammed treatment steps of any information/hardware of the patient treatment module. Optionally, the internal pendant 1218 replaceably mounts to a bracket, hook, slot, or the like mounted on the nozzle system 146 or the beam transport system 135 to maintain close access for the operator when not in use. The operator optionally and preferably uses, at times, a mobile control pendant, such as the external pendant 1216 or the internal pendant 1218. The operator optionally has access via a direct doorway 1229 between treatment room 1222 and the control room 1224. Use of multiple patient interface controllers 1210 gives flexibility to an operator of the motion control system 1200, as further described infra.

EXAMPLE I

In a first example, the operator of the motion control system 1200 is optionally seated or standing by a fixed position controller, such as by a desktop or wall mounted version of the external motion control system 1212. Similarly, the internal motion control system 1214 is optionally and preferably in a fixed position, such as at a desktop system or wall mounted system.

EXAMPLE II

In a second example, the operator optionally and preferably uses, at times, the external pendant 1216, which allows the operator to view the patient 730, the beam transport system 135, the patient interface module 150, and/or the imaging system 170 through the safety of the window 1228. Optionally and preferably, the beam transport system 135 is configured with one or more mechanical stops to not allow the charged particle beam to aim at the window 1228, thereby providing a continuously safe zone for the operator. Direct viewing and control of the charged particle beam system 100, imaging system 170, and/or tomography system 700 relative to the current position of the patient 730 allows backup security in terms of unexpected aim of a treatment beam and/or movement of the patient 730. Controlled elements and/or processes of the charged particle beam system 100 via the pendants is further described, infra.

EXAMPLE III

In a third example, the operator optionally and preferably uses, at times, the internal pendant 1218, which allows the operator both direct access and view of: (1) the patient 730, (2) the beam transport system 135, (3) the patient interface module 150, and/or (4) the imaging system 170, which has multiple benefits. In a first case, the operator can adjust any element of the patient interface module 150, such as a patient positioning device and/or patient motion constraint device. In a second case, the operator has access to load/unload: (1) the patient specific tray insert 510 into the beam control tray assembly 400; (2) the beam control tray assembly 400 into the nozzle system 146, as described supra; and/or (3) any imaging material, such as an X-ray film.

EXAMPLE IV

In a fourth example, the gantry comprises at least two imaging devices, where each imaging device moves with rotation of the gantry and where the two imaging devices view the patient 730 along two axes forming an angle of ninety degrees, in the range of eighty-five to ninety-five degrees, and/or in the range of seventy-five to one hundred five degrees.

Pendant

Referring still to FIG. 12A and referring now to FIG. 12B, a pendant system 1250, such as a system using the external pendant 1216 and/or internal pendent 1218 is described. In a first case, the external pendant 1216 and internal pendant 1218 have identical controls. In a second case, controls and/or functions of the external pendant 1216 intersect with controls and/or function of the internal pendant 1218. Particular processes and functions of the internal pendant 1218 are provided below, without loss of generality, to facilitate description of the external and internal pendants 1216, 1218. The internal pendant 1218 optionally comprises any number of input buttons, screens, tabs, switches, or the like. The pendant system 1250 is further described, infra.

EXAMPLE I

Referring now to FIG. 12B, a first example of the internal pendant 1218 is provided. In this example, in place of and/or in conjunction with a particular button, such as a first button 1270 and/or a second button 1280, moving or selecting a particular element, processes are optionally described, displayed, and/or selected within a flow process control unit 1260 of the internal pendant 1218. For example, one or more display screens and/or printed elements describe a set of processes, such as a first process 1261, a second process 1263, a third process 1265, and a fourth process 1267 and are selected through a touch screen selection process or via a selection button, such as a corresponding first selector 1262, second selector 1264, third selector 1266, and fourth selector 1268. Optionally, a next button a-priori or previously scheduled in treatment planning to select a next process is lit up on the pendant.

EXAMPLE II

Referring still to FIG. 12B, a second example of the internal pendant 1218 is provided. In this example, one or more buttons or the like, such as the first button 1270, and/or one or more of the processes, such as the first process 1261, are customizable, such as to an often repeated set of steps and/or to steps particular to treatment of a given patient 730. The customizable element, such as the first button 1270, is optionally further setup, programmed, controlled, and/or limited via information received from the patient treatment module 1290. In this example, a button, or the like, operates as an emergency all stop button, which at the minimum shuts down the accelerator, redirects the charged particle beam to a beam stop separate from a path through the patient, or stops moving the patient 730.

EXAMPLE III

In place of and/or in conjunction with a particular button, such as the first button 1270 and/or the second button 1280, moving or selecting a particular element, processes are optionally described, displayed, and/or selected within a flow process control unit 1260 of the internal pendant 1218. For example, one or more display screens and/or printed elements describe a set of processes, such as a first process 1261, a second process 1263, a third process 1265, and a fourth process 1267 and are selected through a touch screen selection process or via a selection button, such as a corresponding first selector 1262, second selector 1264, third selector 1266, and fourth selector 1268.

Referring still to FIG. 12B, as illustrated for clarity and without loss or generalization, the first process 1261 and/or a display screen thereof operable by the first selector 1262 selects, initiates, and/or processes a set of steps related to the beam control tray assembly 400. For instance, the first selector 1262, functioning as a tray button: (1) confirms presence a requested patient specific tray insert 510 in a requested tray assembly; (2) confirms presence of a request patient specific tray insert in a receiving slot of the control tray assembly; (3) retracts the beam control tray assembly 400 into the nozzle system 146; (4) confirms information using the electromechanical identifier plug, such as the first electromechanical identifier plug 530; (5) confirms information using the patient treatment module 1290; and/or (6) performs a set of commands and/or movements identified with the first selector 1262 and/or identified with the first process 1261. Similarly, the second process 1263, corresponding to a second process display screen and/or the second selector 1264; the third process 1265, corresponding to a third process display screen and/or the third selector 1266; and the fourth process 1267, corresponding to a fourth process display screen and/or the fourth selector 1268 control and/or activate a set of actions, movements, and/or commands related to positioning the patient 730, imaging the patient 730, and treating the patient 730, respectively.

Integrated Cancer Treatment—Imaging System

One or more imaging systems 170 are optionally used in a fixed position in a cancer treatment room and/or are moved with a gantry system, such as a gantry system supporting: a portion of the beam transport system 135, the targeting/delivery control system 140, and/or moving or rotating around a patient positioning system, such as in the patient interface module. Without loss of generality and to facilitate description of the invention, examples follow of an integrated cancer treatment—imaging system. In each system, the beam transport system 135 and/or the nozzle system 146 indicates a positively charged beam path, such as from the synchrotron, for tumor treatment and/or for tomography, as described supra.

EXAMPLE I

Figure 13A:
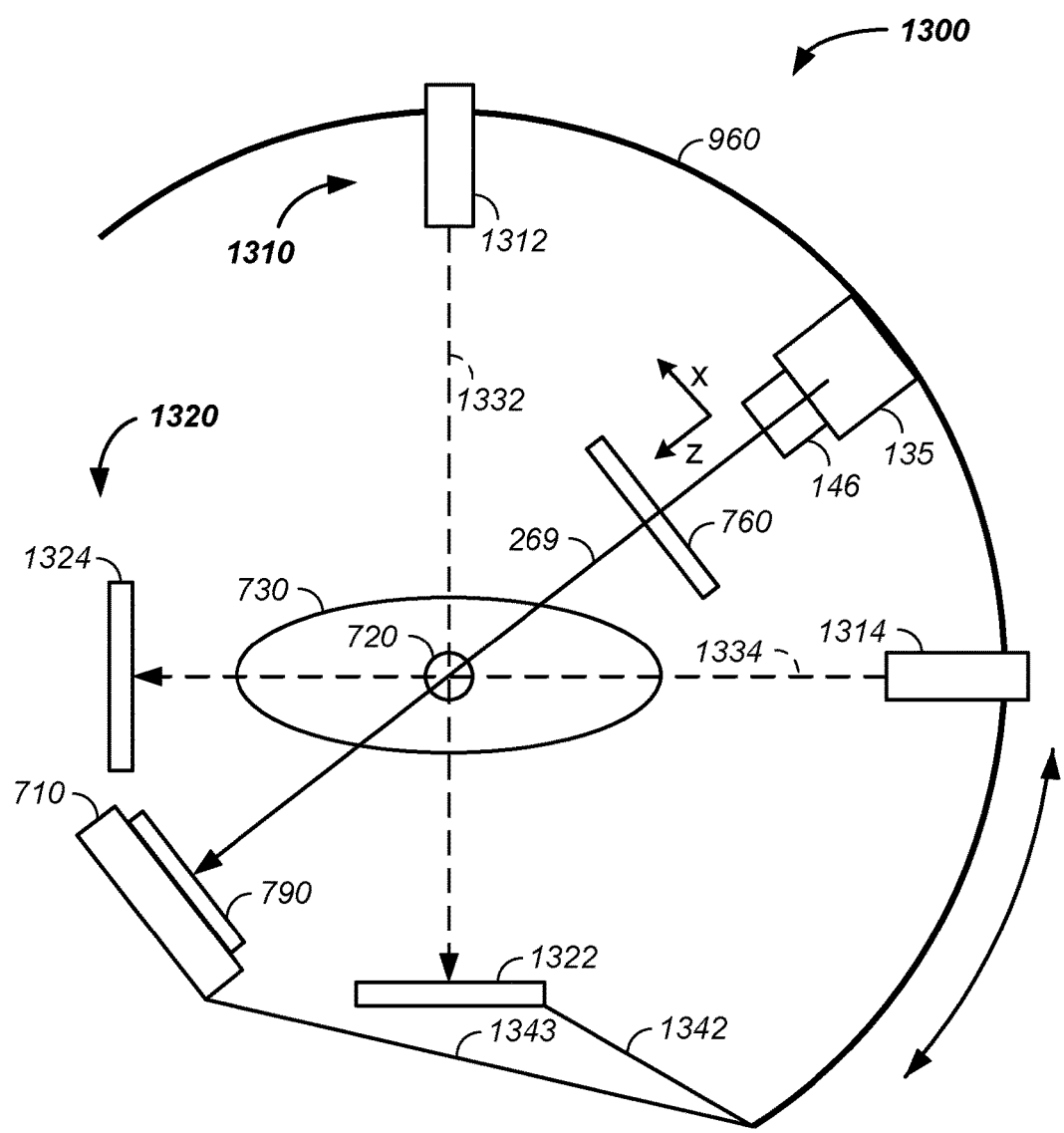
FIG. 13A illustrates a two-dimensional-two-dimensional imaging system relative to a cancer treatment beam.

Referring now to FIG. 13A, a first example of an integrated cancer treatment—imaging system 1300 is illustrated. In this example, the charged particle beam system 100 is illustrated with a treatment beam 269 directed to the tumor 720 of the patient 730 along the z-axis. Also illustrated is a set of imaging sources 1310, imaging system elements, and/or paths therefrom and a set of detectors 1320 corresponding to a respective element of the set of imaging sources 1310. Herein, the set of imaging sources 1310 are referred to as sources, but are optionally any point or element of the beam train prior to the tumor or a center point about which the gantry rotates. Hence, a given imaging source is optionally a dispersion element used to for cone beam. As illustrated, a first imaging source 1312 yields a first beam path 1332 and a second imaging source 1314 yields a second beam path 1334, where each path passes at least into the tumor 720 and optionally and preferably to a first detector array 1322 and a second detector array 1324, respectively, of the set of detectors 1320. Herein, the first beam path 1332 and the second beam path 1334 are illustrated as forming a ninety degree angle, which yields complementary images of the tumor 720 and/or the patient 730. However, the formed angle is optionally any angle from ten to three hundred fifty degrees. Herein, for clarity of presentation, the first beam path 1332 and the second beam path 1334 are illustrated as single lines, which optionally is an expanding, uniform diameter, or focusing beam. Herein, the first beam path 1332 and the second beam path 1334 are illustrated in transmission mode with their respective sources and detectors on opposite sides of the patient 730. However, a beam path from a source to a detector is optionally a scattered path and/or a diffuse reflectance path. Optionally, one or more detectors of the set of detectors 1320 are a single detector element, a line of detector elements, or preferably a two-dimensional detector array. Use of two two-dimensional detector arrays is referred to herein as a two-dimensional-two-dimensional imaging system or a 2D-2D imaging system.

Still referring to FIG. 13A, the first imaging source 1312 and the second imaging source 1314 are illustrated at a first position and a second position, respectively. Each of the first imaging source 1312 and the second imaging source 1322 optionally: (1) maintain a fixed position; (2) provide the first beam path 1332 and the second beam path 1334, respectively, through the gantry 960, such as through a set of one or more holes or slits; (3) provide the first beam path 1332 and the second beam path 1334, respectively, off axis to a plane of movement of the nozzle system 760; (4) move with the gantry 960 as the gantry 960 rotates about at least a first axis; and/or (5) represent a narrow cross-diameter section of an expanding cone beam path.

Still referring to FIG. 13A, the set of detectors 1320 are illustrated as coupling with respective elements of the set of sources 1310. Each member of the set of detectors 1320 optionally and preferably co-moves/and/or co-rotates with a respective member of the set of sources 1310. Thus, if the first imaging source 1312 is statically positioned, then the first detector 1322 is optionally and preferably statically positioned. Similarly, to facilitate imaging, if the first imaging source 1312 moves along a first arc as the gantry 960 moves, then the first detector 1322 optionally and preferably moves along the first arc or a second arc as the gantry 960 moves, where relative positions of the first imaging source 1312 on the first arc, a point that the gantry 960 moves about, and relative positions of the first detector 1322 along the second arc are constant. To facilitate the process, the detectors are optionally mechanically linked, such as with a first mechanical support 1342 to the gantry 960 in a manner that when the gantry 960 moves, the gantry moves both the source and the corresponding detector. Optionally, the source moves and a series of detectors, such as along the second arc, capture a set of images.

Still referring to FIG. 13A, optionally and preferably, elements of the set of sources 1310 combined with elements of the set of detectors 1320 are used to collect a series of responses, such as one source and one detector yielding a detected intensity and preferably a set of detected intensities to form an image. For instance, the first imaging source 1312, such as a first X-ray source or first cone beam X-ray source, and the first detector 1322, such as an X-ray film, digital X-ray detector, or two-dimensional detector, yield a first X-ray image of the patient at a first time and a second X-ray image of the patient at a second time, such as to confirm a maintained location of a tumor or after movement of the gantry 760 or rotation of the patient 730. A set of n images using the first imaging source 1312 and the first detector 1322 collected as a function of movement of the gantry 760 and/or as a function of movement and/or rotation of the patient 730 are optionally and preferably combined to yield a three-dimensional image of the patient 730, such as a three-dimensional X-ray image of the patient 730, where n is a positive integer, such as greater than 1, 2, 3, 4, 5, 10, 15, 25, 50, or 100. The set of n images is optionally gathered as described in combination with images gathered using the second imaging source 1314, such as a second X-ray source or second cone beam X-ray source, and the second detector 1324, such as a second X-ray detector, where the use of two, or multiple, source/detector combinations are combined to yield images where the patient 730 has not moved between images as the two, or the multiple, images are optionally and preferably collected at the same time, such as with a difference in time of less than 0.01, 0.1, 1, or 5 seconds. Longer time differences are optionally used. Preferably the n two-dimensional images are collected as a function of rotation of the gantry 960 about the tumor and/or the patient and/or as a function of rotation of the patient 730 and the two-dimensional images of the X-ray cone beam are mathematically combined to form a three-dimensional image of the tumor 720 and/or the patient 730. Optionally, the first X-ray source and/or the second X-ray source is the source of X-rays that are divergent forming a cone through the tumor. A set of images collected as a function of rotation of the divergent X-ray cone around the tumor with a two-dimensional detector that detects the divergent X-rays transmitted through the tumor is used to form a three-dimensional X-ray of the tumor and of a portion of the patient, such as in X-ray computed tomography.

Still referring to FIG. 13A, use of two imaging sources and two detectors set at ninety degrees to one another allows the gantry 960 or the patient 730 to rotate through half an angle required using only one imaging source and detector combination. A third imaging source/detector combination allows the three imaging source/detector combination to be set at sixty degree intervals allowing the imaging time to be cut to that of one-third that gantry 960 or patient 730 rotation required using a single imaging source-detector combination. Generally, n source-detector combinations reduces the time and/or the rotation requirements to 1/n. Further reduction is possible if the patient 730 and the gantry 960 rotate in opposite directions. Generally, the used of multiple source-detector combination of a given technology allow for a gantry that need not rotate through as large of an angle, with dramatic engineering benefits.

Still referring to FIG. 13A, the set of sources 1310 and set of detectors 1320 optionally use more than one imaging technology. For example, a first imaging technology uses X-rays, a second used fluoroscopy, a third detects fluorescence, a fourth uses cone beam computed tomography or cone beam CT, and a fifth uses other electromagnetic waves. Optionally, the set of sources 1310 and the set of detectors 1320 use two or more sources and/or two or more detectors of a given imaging technology, such as described supra with two X-ray sources to n X-ray sources.

Still referring to FIG. 13A, use of one or more of the set of sources 1310 and use of one or more of the set of detectors 1320 is optionally coupled with use of the positively charged particle tomography system described supra. As illustrated in FIG. 13A, the positively charged particle tomography system uses a second mechanical support 1343 to co-rotate the scintillation plate 710 with the gantry 960, as well as to co-rotate an optional sheet, such as the first sheet 760 and/or the fourth sheet 790.

EXAMPLE II

Referring now to FIG. 13B, a second example of the integrated cancer treatment—imaging system 1300 is illustrated using greater than three imagers.

Still referring to FIG. 13B, two pairs of imaging systems are illustrated. Particularly, the first and second imaging source 1312, 1314 coupled to the first and second detectors 1322, 1324 are as described supra. For clarity of presentation and without loss of generality, the first and second imaging systems are referred to as a first X-ray imaging system and a second X-ray imaging system. The second pair of imaging systems uses a third imaging source 1316 coupled to a third detector 1326 and a fourth imaging source 1318 coupled to a fourth detector 1328 in a manner similar to the first and second imaging systems described in the previous example. Here, the second pair of imaging systems optionally and preferably uses a second imaging technology, such as fluoroscopy. Optionally, the second pair of imaging systems is a single unit, such as the third imaging source 1318 couple to the third detector 1328, and not a pair of units. Optionally, one or more of the set of imaging sources 1310 are statically positioned while one of more of the set of imaging sources 1310 co-rotate with the gantry 960. Pairs of imaging sources/detector optionally have common and distinct distances, such as a first distance, $d_1$, such as for a first source-detector pair and a second distance, $d_2$, such as for a second source-detector or second source-detector pair. As illustrated, the tomography detector or the scintillation plate 710 is at a third distance, $d_3$. The distinct differences allow the source-detector elements to rotate on a separate rotation system at a rate different from rotation of the gantry 960, which allows collection of a full three-dimensional image while tumor treatment is proceeding with the positively charged particles.

EXAMPLE III

For clarity of presentation, referring now to FIG. 13C, any of the beams or beam paths described herein is optionally a cone beam 1390 as illustrated. The patient support 152 is an mechanical and/or electromechanical device used to position, rotate, and/or constrain any portion of the tumor 720 and/or the patient 730 relative to any axis.

Still yet another embodiment includes any combination and/or permutation of any of the elements described herein.

Herein, any number, such as 1, 2, 3, 4, 5, is optionally more than the number, less than the number, or within 1, 2, 5, 10, 20, or 50 percent of the number.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for determination of a state of positively charged particles of a charged particle beam entering a patient along a beam path, comprising the steps of:
using a beam transport system to transport the positively charged particles from a synchrotron to an exit nozzle,
a slideably insertable beam insert positioned proximate said exit nozzle;
reshaping the charged particle beam using the beam insert;
positioning a first imaging sheet in the beam path between said beam insert and the patient; and
imaging first photons emitted from said first imaging sheet using a detector system, wherein, resultant from transmission of the positively charged particles transmitting through said first imaging sheet, said first imaging sheet emits the first photons;
positioning a second imaging sheet in the beam path between said first imaging sheet and the patient; and
imaging second photons emitted from said second imaging sheet using said detector system, wherein, resultant from transmission of the positively charged particle transmitting through said second imaging sheet, said second imaging sheet emits the second photons; and
further comprising the step of:
verifying direction of the beam path against a radiation treatment plan using two signals from said detector system, said two signals comprising a first position signal representative of a first location of the first photons emitted from said first imaging sheet and a second position signal representative of a second location of the second photons emitted from the second imaging sheet.

2. The method of claim 1, further comprising the step of:
verifying position of the charged particle beam against a radiation treatment plan for the patient using a signal from said detector system resultant from the first photons.

3. The method of claim 2, further comprising the step of:
verifying intensity of the charged particle beam against the radiation treatment plan using an intensity of the signal.

4. The method of claim 1, further comprising the step of:
determining a beam path vector using a first detected location of the first photons and a second detected location of the second photons in tomographic reconstruction of a three-dimensional image of the tumor.

5. The method of claim 1, said step of reshaping further comprising the step of:
changing a focal point of the charged particle beam using said beam insert, said beam insert comprising a ridge filter.

6. The method of claim 1, further comprising the step of:
said detector system detecting: (1) the first photons at a first wavelength and (2) the second photons at a second wavelength, said first imaging sheet at least one centimeter from said second imaging sheet in the beam path.

7. The method of claim 6, the second wavelength at least fifty nanometers greater than the first wavelength.

8. The method of claim 1, further comprising the step of:
moving both said exit nozzle and said imaging sheet with a gantry; and
during said step of moving, maintaining a relative orientation of a detection element of said detection system, said first imaging sheet, and said exit nozzle.

9. The method of claim 8, further comprising the steps of:
using said detection system to determine: (1) a first position of emission of said first photons and (2) a second position of emission of the second photons; and
using the first position and the second position as input data for a step of a three-dimensional tomographic image construction of the tumor.

10. The method of claim 9, further comprising the step of:
detecting a position of the positively charged particles after transmitting through the tumor using a detection element.

11. An apparatus for determination of a state of positively charged particles of a charged particle beam entering a patient along a beam path, comprising:

a beam transport system configured to transport the positively charged particles from a synchrotron to an exit nozzle;

a slideably insertable beam insert positioned proximate said exit nozzle;

a first imaging sheet positioned in the beam path between the beam insert and the patient during use; and a detector system configured to image said first imaging sheet, said first imaging sheet configured to emit first photons upon transmission of the positively charged particles through said first imaging sheet;

a second imaging sheet positioned between said first imaging sheet and the patient during use, said first imaging sheet at least one centimeter from said second imaging sheet in the beam path, said second imaging sheet configured to locally emit second photons upon passage of the positively charged particles; and verifying direction of the beam path against a radiation treatment plan using two signals from said detector system, said two signals comprising a first position signal representative of a first location of the first photons emitted from said first imaging sheet and a second position signal representative of a second location of the second photons emitted from the second imaging sheet.

12. The apparatus of claim 11, said detector system further comprising:

a first detector array optically coupled to said first imaging sheet; and a second detector array optically coupled to said second imaging sheet.

13. The apparatus of claim 11, further comprising:

a first optically coupled path of the first photons to said detector system; and a second optically coupled path of the second photons to said detector system, said second optically coupled path comprising an absorbance filter, said absorbance filter comprising an absorbance of greater than fifty percent of photons at a first wavelength of said first photons.

14. The apparatus of claim 11, further comprising:

a tomographic imaging detection element positioned on an opposite side of said first imaging sheet from said beam insert.

15. The apparatus of claim 14, further comprising:

a gantry configured to co-rotate about an axis all of: said tomographic imaging detection element, said first imaging sheet, and said beam insert.

16. An apparatus for determination of a state of positively charged particles of a charged particle beam entering a patient along a beam path, comprising:

a beam transport system configured to transport the positively charged particles from a synchrotron to an exit nozzle;

a slideably insertable beam insert positioned proximate said exit nozzle;

a first imaging sheet positioned in the beam path between the beam insert and the patient during use; and a detector system configured to image said first imaging sheet, said first imaging sheet configured to emit first photons upon transmission of the positively charged particles through said first imaging sheet; and further comprising:

a second imaging sheet positioned between said first imaging sheet and said tomographic imaging detection element, said second imaging sheet configured to emit second photons upon transmission of the positively charged particles through said second imaging sheet; and verifying direction of the beam path against a radiation treatment plan using two signals from said detector system, said two signals comprising a first position signal representative of a first location of the first photons emitted from said first imaging sheet and a second position signal representative of a second location of the second photons emitted from the second imaging sheet.

17. The apparatus of claim 16, said tomographic imaging detection element comprising a scintillation material.

\* \* \* \* \*